(12) United States Patent
Justin et al.

(10) Patent No.: US 7,618,459 B2
(45) Date of Patent: Nov. 17, 2009

(54) UNIVERSAL SPINAL DISC IMPLANT SYSTEM

(75) Inventors: Daniel F. Justin, Logan, UT (US); Lytton A. Williams, Los Angeles, CA (US); Darin R. Ewer, Providence, UT (US); Nathan Pierce, Millville, UT (US)

(73) Assignee: Infinity Orthopedics Ltd., Ianling N.T. (HK)

( * ) Notice: Subject to any disclaimer, the term of this patent is extended or adjusted under 35 U.S.C. 154(b) by 0 days.

(21) Appl. No.: 11/534,985

(22) Filed: Sep. 25, 2006

(65) Prior Publication Data

US 2007/0072475 A1 Mar. 29, 2007

Related U.S. Application Data

(60) Provisional application No. 60/720,513, filed on Sep. 26, 2005, provisional application No. 60/720,514, filed on Sep. 26, 2005, provisional application No. 60/741,513, filed on Nov. 30, 2005.

(51) Int. Cl.
*A61F 2/44* (2006.01)
(52) U.S. Cl. .................. 623/17.15; 623/17.11
(58) Field of Classification Search .............. 623/16.11, 623/17.11–17.16
See application file for complete search history.

(56) References Cited

U.S. PATENT DOCUMENTS

| | | |
|---|---|---|
| 3,875,595 A | 4/1975 | Froning |
| 4,309,777 A | 1/1982 | Patil |
| 4,349,921 A | 9/1982 | Kuntz |
| 4,401,112 A | 8/1983 | Rezaian |
| 4,501,269 A | 2/1985 | Bagby |
| 4,553,273 A | 11/1985 | Wu |
| 4,554,914 A | 11/1985 | Kapp |

(Continued)

FOREIGN PATENT DOCUMENTS

EP 188954 A1 7/1986

(Continued)

OTHER PUBLICATIONS

Andre Van Ooij, *Complications of Artificial Disc Replacement*; Journal of Spinal Disorders, vol. 16, No. 4, pp. 369-385 (2003).

*Primary Examiner*—Eduardo C Robert
*Assistant Examiner*—Tara R George
(74) *Attorney, Agent, or Firm*—David W. Meibos; Barbara Daniels; Daniel E. Justin

(57) ABSTRACT

A revisable intervertebral implant may include two end plates designed to detachably receive a variety of intermediate components including articulating bearing inserts, elastic inserts, and fusion blocks. Each intermediate component may be secured to a snap insert that snaps into engagement with the corresponding end plate in response to pressure urging the intermediate component toward the end plate along a cephalad-caudal direction. The end plates may first be secured to the corresponding vertebral bodies, and then the intermediate component(s) may be snapped into locking engagement with the implanted end plates to complete in-situ assembly of the intervertebral implant. The implant may easily be revised by snapping the intermediate component(s) out of engagement with the end plates, removing the intermediate component(s), inserting the new intermediate component(s) into the space between the end plates, and snapping the new intermediate component(s) into engagement with the end plates.

39 Claims, 26 Drawing Sheets

U.S. PATENT DOCUMENTS

| | | | |
|---|---|---|---|
| 4,599,086 A | 7/1986 | Doty | |
| 4,627,853 A | 12/1986 | Campbell | |
| 4,636,217 A | 1/1987 | Ogilvie | |
| 4,678,470 A | 7/1987 | Nashef | |
| 4,714,469 A | 12/1987 | Kenna | |
| 4,743,256 A | 5/1988 | Brantigan | |
| 4,743,259 A | 5/1988 | Bolander | |
| 4,759,766 A | 7/1988 | Buettner-Janz et al. | |
| 4,759,769 A | 7/1988 | Hedman | |
| 4,834,757 A | 5/1989 | Brantigan | |
| 4,863,476 A | 9/1989 | Shepperd | |
| 4,878,915 A | 11/1989 | Brantigan | |
| 4,892,545 A | 1/1990 | Day | |
| 4,932,975 A | 6/1990 | Main | |
| 4,961,740 A | 10/1990 | Ray | |
| 4,997,432 A | 3/1991 | Keller | |
| 5,015,247 A | 5/1991 | Michelson | |
| 5,026,373 A | 6/1991 | Ray | |
| 5,055,104 A | 10/1991 | Ray | |
| 5,059,193 A | 10/1991 | Kuslich | |
| 5,062,850 A | 11/1991 | MacMillan | |
| 5,071,437 A | 12/1991 | Steffee | |
| 5,123,926 A | 6/1992 | Pisharodi | |
| 5,147,402 A | 9/1992 | Bohler | |
| 5,192,327 A | 3/1993 | Brantigan | |
| 5,236,460 A | 8/1993 | Barber | |
| 5,258,031 A | 11/1993 | Salib | |
| 5,263,953 A | 11/1993 | Bagby | |
| 5,290,312 A | 3/1994 | Kojimoto | |
| 5,306,310 A | 4/1994 | Siebels | |
| 5,314,477 A | 5/1994 | Marnay | |
| 5,336,223 A | 8/1994 | Rogers | |
| 5,370,697 A | 12/1994 | Baumgartner | |
| 5,397,364 A | 3/1995 | Kozak | |
| 5,401,269 A | 3/1995 | Buttner-Janz | |
| 5,417,975 A | 5/1995 | Lussi | |
| 5,425,769 A | 6/1995 | Snyders, Jr. | |
| 5,425,773 A | 6/1995 | Boyd | |
| 5,439,684 A | 8/1995 | Prewett | |
| 5,455,231 A | 10/1995 | Constantz | |
| 5,458,641 A | 10/1995 | Ramirez Jimenez | |
| 5,464,439 A | 11/1995 | Gendler | |
| 5,480,442 A | 1/1996 | Bertagnoli | |
| 5,507,813 A | 4/1996 | Dowd | |
| 5,507,816 A | 4/1996 | Bullivant | |
| 5,510,396 A | 4/1996 | Prewett | |
| 5,522,899 A | 6/1996 | Michelson | |
| 5,534,030 A | 7/1996 | Navarro | |
| 5,549,679 A | 8/1996 | Kuslich | |
| 5,554,191 A | 9/1996 | Lahille | |
| 5,556,431 A | 9/1996 | Buttner-Janz | |
| 5,562,738 A | 10/1996 | Boyd et al. | |
| 5,585,116 A | 12/1996 | Boniface | |
| 5,609,635 A | 3/1997 | Michelson | |
| 5,645,591 A | 7/1997 | Kuberasampath | |
| 5,653,763 A | 8/1997 | Errico | |
| 5,658,335 A | 8/1997 | Allen | |
| 5,665,122 A | 9/1997 | Kambin | |
| 5,676,701 A | 10/1997 | Yuan | |
| 5,683,465 A | 11/1997 | Shinn | |
| 5,693,100 A | 12/1997 | Pisharodi | |
| 5,702,391 A | 12/1997 | Lin | |
| 5,702,450 A | 12/1997 | Bisserie | |
| 5,702,453 A | 12/1997 | Rabbe | |
| 5,702,455 A | 12/1997 | Saggar | |
| 5,713,904 A | 2/1998 | Errico | |
| 5,749,916 A | 5/1998 | Richelsoph | |
| 5,776,197 A | 7/1998 | Rabbe | |
| 5,776,199 A | 7/1998 | Michelson | |
| 5,782,832 A | 7/1998 | Larsen | |
| 5,800,550 A | 9/1998 | Sertich | |
| 5,888,227 A | 3/1999 | Cottle | |
| 5,895,428 A | 4/1999 | Berry | |
| 5,899,941 A | 5/1999 | Nishijima | |
| 5,916,267 A | 6/1999 | Tienboon | |
| 5,980,522 A | 11/1999 | Koros et al. | |
| 5,989,290 A | 11/1999 | Biedermann | |
| 6,015,436 A | 1/2000 | Schonhoffer | |
| 6,019,792 A | 2/2000 | Cauthen | |
| 6,039,763 A | 3/2000 | Shelokov | |
| 6,045,579 A | 4/2000 | Hochshuler | |
| 6,080,193 A | 6/2000 | Hochshuler | |
| 6,102,950 A | 8/2000 | Vaccaro | |
| 6,106,557 A | 8/2000 | Robioneck | |
| 6,113,637 A | 9/2000 | Gill et al. | |
| 6,113,638 A | 9/2000 | Williams | |
| 6,146,421 A | 11/2000 | Gordon et al. | |
| 6,176,881 B1 | 1/2001 | Schar | |
| 6,176,882 B1 | 1/2001 | Biedermann et al. | |
| 6,179,874 B1 | 1/2001 | Cauthen | |
| 6,217,579 B1 | 4/2001 | Koros | |
| 6,228,118 B1 | 5/2001 | Gordon | |
| 6,344,057 B1 | 2/2002 | Rabbe | |
| 6,375,681 B1 | 4/2002 | Truscott | |
| 6,375,683 B1 | 4/2002 | Crozet | |
| 6,402,785 B1 | 6/2002 | Zdeblick | |
| 6,419,704 B1 | 7/2002 | Ferree | |
| 6,440,168 B1 | 8/2002 | Cauthen | |
| 6,517,580 B1 | 2/2003 | Ramadan et al. | |
| 6,524,641 B1 | 2/2003 | de Witzmann | |
| 6,540,785 B1 | 4/2003 | Gill et al. | |
| 6,576,016 B1 | 6/2003 | Hochshuler et al. | |
| 6,641,614 B1 | 11/2003 | Wagner et al. | |
| 6,679,915 B1 | 1/2004 | Cauthen | |
| 6,706,070 B1 | 3/2004 | Wagner et al. | |
| 6,726,720 B2 | 4/2004 | Ross et al. | |
| 6,800,092 B1 | 10/2004 | Williams et al. | |
| 6,899,735 B2 | 5/2005 | Coates et al. | |
| 6,986,789 B2 * | 1/2006 | Schultz et al. | 623/17.15 |
| 7,115,144 B2 * | 10/2006 | Diaz et al. | 623/17.14 |
| 2002/0161441 A1 | 10/2002 | Lang | |
| 2003/0187454 A1 | 10/2003 | Gill et al. | |
| 2003/0208272 A1 | 11/2003 | Crozet | |
| 2004/0010316 A1 | 1/2004 | Williams et al. | |
| 2004/0260396 A1 | 12/2004 | Ferree et al. | |
| 2005/0027362 A1 | 2/2005 | Williams et al. | |
| 2005/0060034 A1 | 3/2005 | Berry et al. | |
| 2005/0187634 A1 * | 8/2005 | Berry | 623/17.15 |
| 2005/0192671 A1 * | 9/2005 | Bao et al. | 623/17.14 |
| 2006/0015183 A1 * | 1/2006 | Gilbert et al. | 623/17.11 |
| 2006/0111783 A1 * | 5/2006 | Aflatoon et al. | 623/17.14 |
| 2006/0149378 A1 * | 7/2006 | Chase et al. | 623/17.11 |
| 2006/0217809 A1 * | 9/2006 | Albert et al. | 623/17.11 |
| 2007/0021837 A1 * | 1/2007 | Ashman | 623/17.16 |

FOREIGN PATENT DOCUMENTS

| | | |
|---|---|---|
| EP | 538183 A1 | 4/1993 |
| EP | 610837 A1 | 8/1994 |
| EP | 425542 B1 | 3/1995 |
| EP | 1161205 A1 | 8/2000 |
| WO | WO9204423 A1 | 9/1992 |
| WO | WO9310725 A2 | 6/1993 |
| WO | WO9404100 A1 | 3/1994 |
| WO | WO9700054 A1 | 1/1997 |
| WO | WO0049977 C2 | 8/2000 |
| WO | WO0217825 A2 | 3/2002 |

* cited by examiner

UNIVERSAL SPINAL DISC IMPLANT SYSTEM

CROSS-REFERENCE TO RELATED APPLICATIONS

This application claims the benefit of the following:

U.S. Provisional Application No. 60,720,513, filed Sep. 26, 2005, which is entitled MODULAR ARTICULATING AND FUSION SPINAL DISC IMPLANT SYSTEM;

U.S. Provisional Application No. 60/720,514, filed Sep. 26, 2005, which is entitled UNIVERSAL SPINAL DISC IMPLANT SYSTEM FOR PROVIDING INTERVERTEBRAL ARTICULATION AND FUSION; and U.S. Provisional Application No. 60/741,513, filed Nov. 30, 2005, which is entitled SYSTEM AND METHOD FOR INTERVERTEBRAL IMPLANT DELIVERY AND REMOVAL.

All of the foregoing are incorporated herein by reference.

BACKGROUND OF THE INVENTION

1. The Field of the Invention

The present invention relates generally to spinal orthopedics, and more precisely, to intervertebral implants.

2. The Relevant Technology

Severe back pain can be caused by a number of different ailments, including spinal stenosis, degenerative disc disease, spondylolisthesis, and the like. Many such ailments can be corrected by controlling or limiting relative motion between the affected vertebrae. Accordingly, a variety of devices including artificial discs and fusion devices have been proposed.

Such devices are limited in that they typically provide only one mode of correction. Many such devices cannot be replaced or corrected. This is particularly true with intervertebral implants, in which bone-growth is often stimulated to integrate the implants with the surrounding bone tissue. Thus, if the device fails to solve the problem, there may be no other recourse for the patient.

Further, many known devices are expensive or difficult to manufacture, or are difficult to implant. Some known intervertebral devices require the adjacent vertebrae to be distracted excessively, thereby endangering the surrounding ligaments and other connective tissues. Accordingly, there is a need in the art for a device that remedies these problems. Such a device would considerably enhance outcomes for patients with spinal disorders.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to human spinal disc replacement systems. Those of skill in the art will recognize that the systems and methods described herein may be readily adapted for other modular implant systems for anatomic replication of orthopedic joints by man made implant systems.

Figure 1:
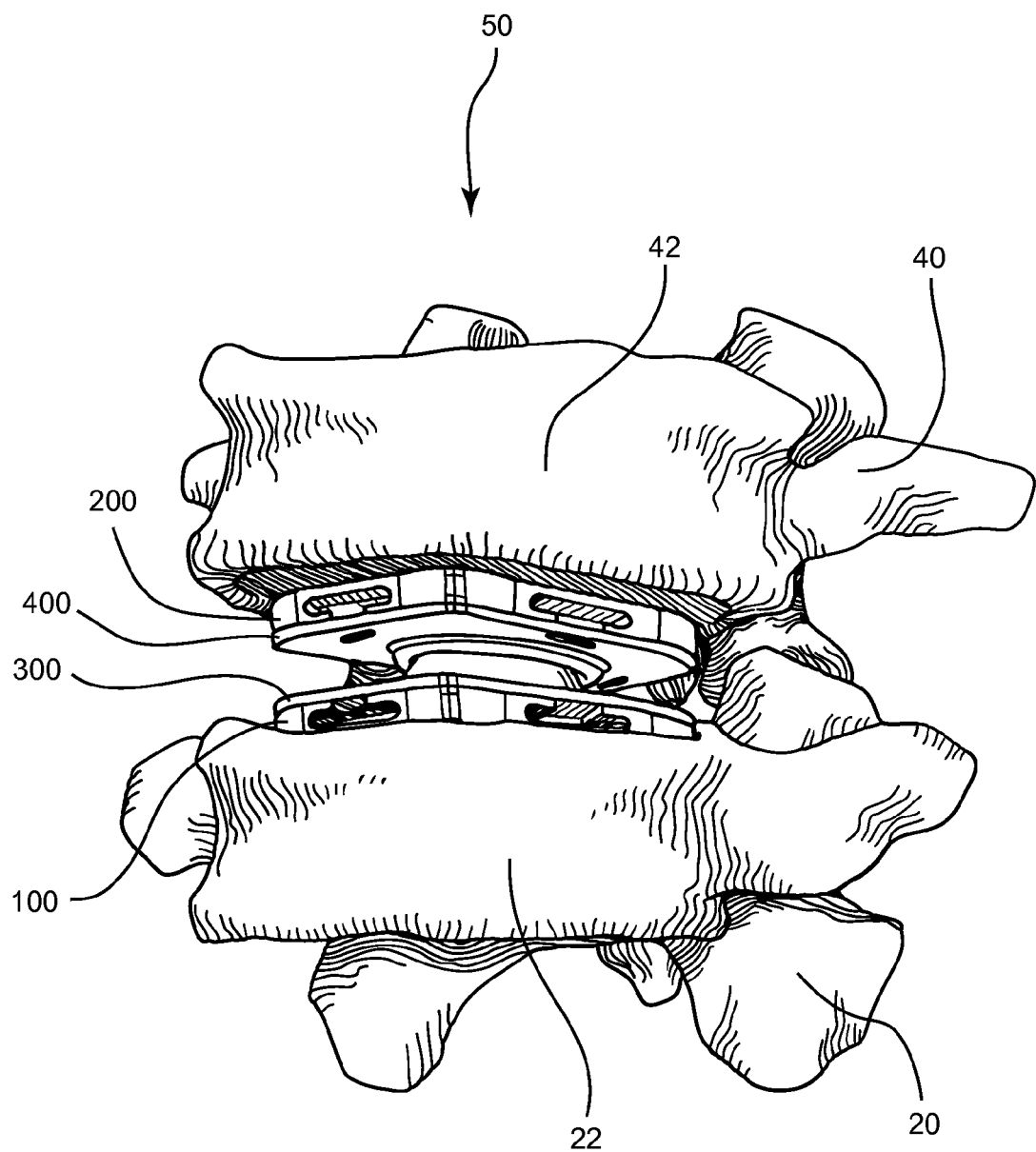
FIG. 1 is a perspective view of the total disc implant in a portion of the spine, according to one embodiment of the invention.

Referring to FIG. 1, a perspective view illustrates one embodiment of an implant 50, which may be referred to as a total disc implant, implanted in a portion of the spine. In this embodiment of the invention, the total disc implant includes two end plates 100, 200, two bearings 300, 400, and two snap fasteners 500 (not visible in FIG. 1) which releasably hold the bearings to the end plates. The implant 50 is designed for placement between spinal vertebrae to replace degenerated intervertebral disk material. More specifically, the implant 50 of FIG. 1 is designed to be inserted between the vertebral bodies 22, 42 of the first and second vertebrae 20, 40, respectively, after removal of the intervertebral disc (not shown). The vertebral bodies 22, 42 are rasped and flat surfaces on them are prepared to fit the end plates 100, 200.

The procedure to implant the total disc implant may be conducted from any of three approaches: anterior, right lateral, or left lateral. In addition, should there be any subsequent procedure for adjustment of the implant 50 or replacement of any component thereof, such procedure may be carried out from any one of the three approaches.

Figure 2:
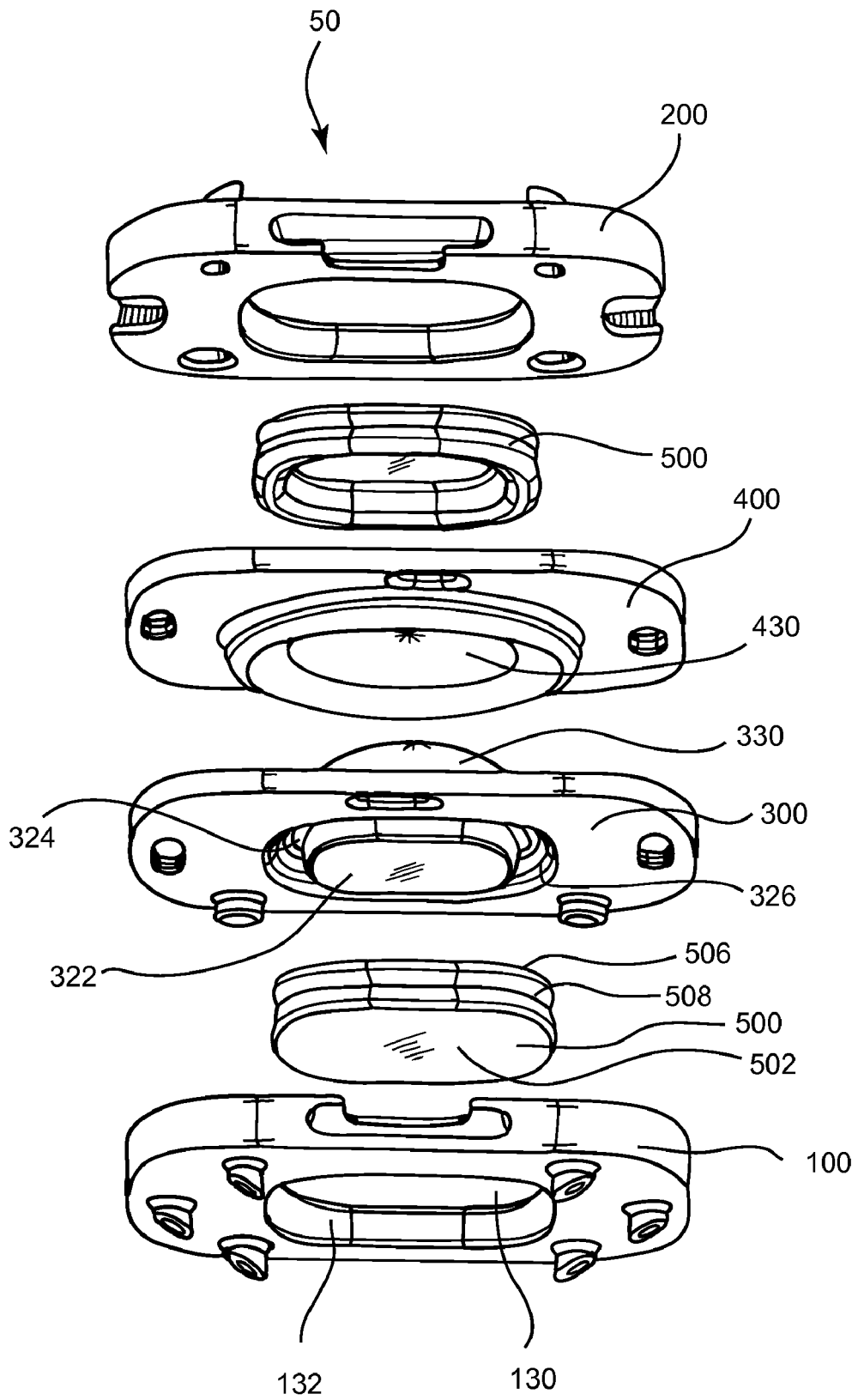
FIG. 2 is a perspective view of the total disc implant shown in FIG. 1 in a disassembled state.

FIG. 2 illustrates the implant 50 in a disassembled state, so that all components are visible. During the implantation procedure, the end plates 100, 200 are pressed into place onto the vertebral bodies, with the inferior end plate 100 in a caudal position on vertebral body 22, and superior end plate 200 in a cephalic position on vertebral body 42. The end plates 100, 200 may be implanted in either order (inferior first or superior first). Once implanted, the two end plates 100, 200 appear as mirror images of one another with their bearing facing sides facing one another. Next, the inferior 300 and superior bearings 400 are attached to the end plates, using the snap fasteners 500 as releasable connectors. A set force delivered by the implantation instrumentation (not shown) presses each snap fastener 500 into place. The inferior bearing 300 is attached to the inferior end plate 100 with one snap fastener 500 between them, and the superior bearing 400 is attached to the superior end plate 200 with another snap fastener 500 between them. Like the end plates, the bearings 300, 400 may also be attached in either order.

Figure 3:
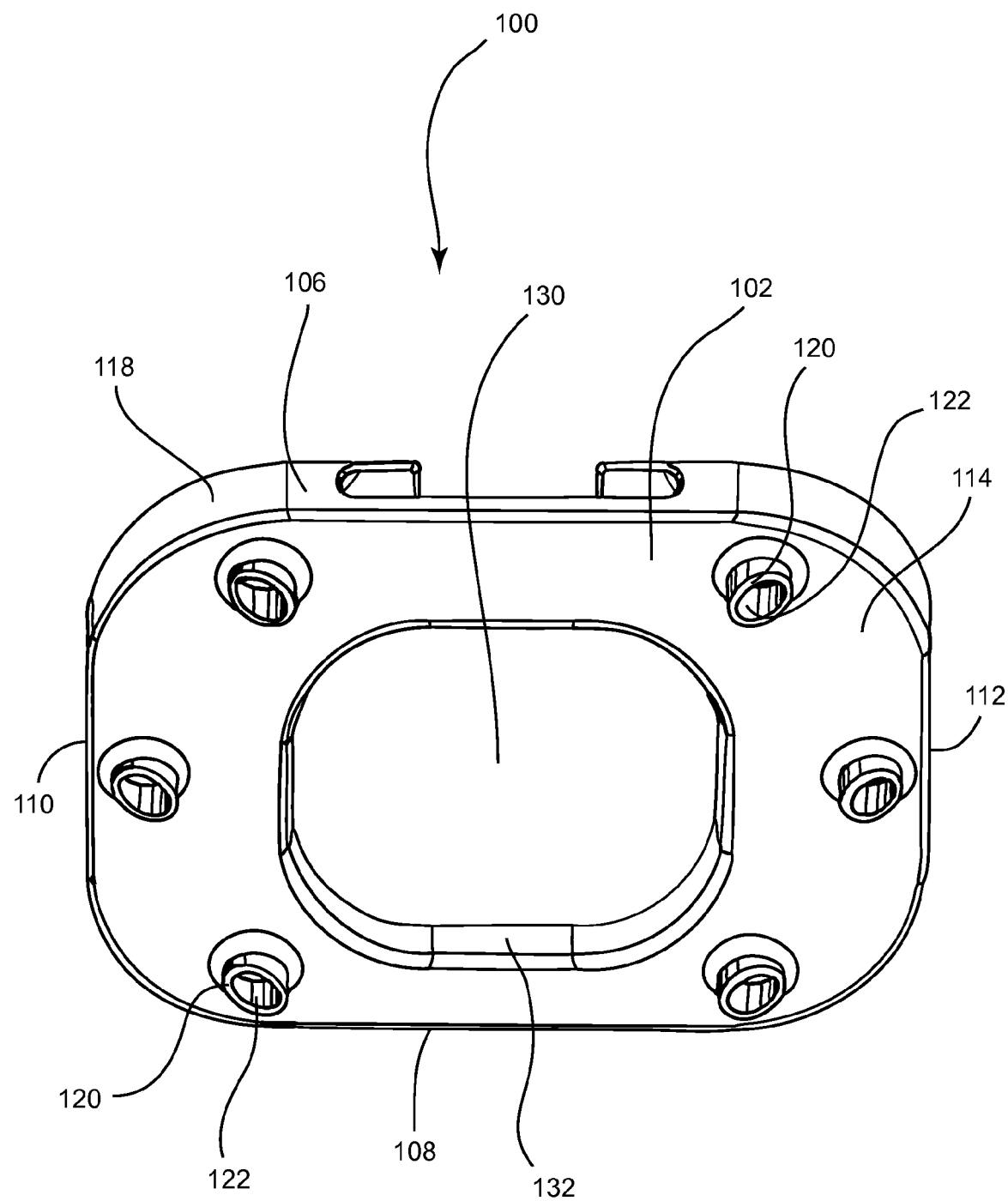
FIG. 3 is a perspective view of the bone-facing side of the inferior end plate shown in FIG. 2.

FIG. 3 illustrates a bone-facing side of one end plate. In the illustration, the end plate depicted is the inferior end plate 100, and so the bone-facing side 102 is in the caudal direction. In this embodiment of the invention the superior end plate 200 is identical to the inferior end plate 100 in every way except in orientation once implanted in the body. Thus, when the superior end plate 200 is implanted, its bone-facing side will be in the cephalic direction. With this exception due to orientation noted, FIGS. 3 and 4 and the description of the end plate below also apply to the superior end plate 200. However, it is appreciated that in alternative embodiments of the invention, the end plates may or may not be identical in size, shape, or configuration.

Figure 4:
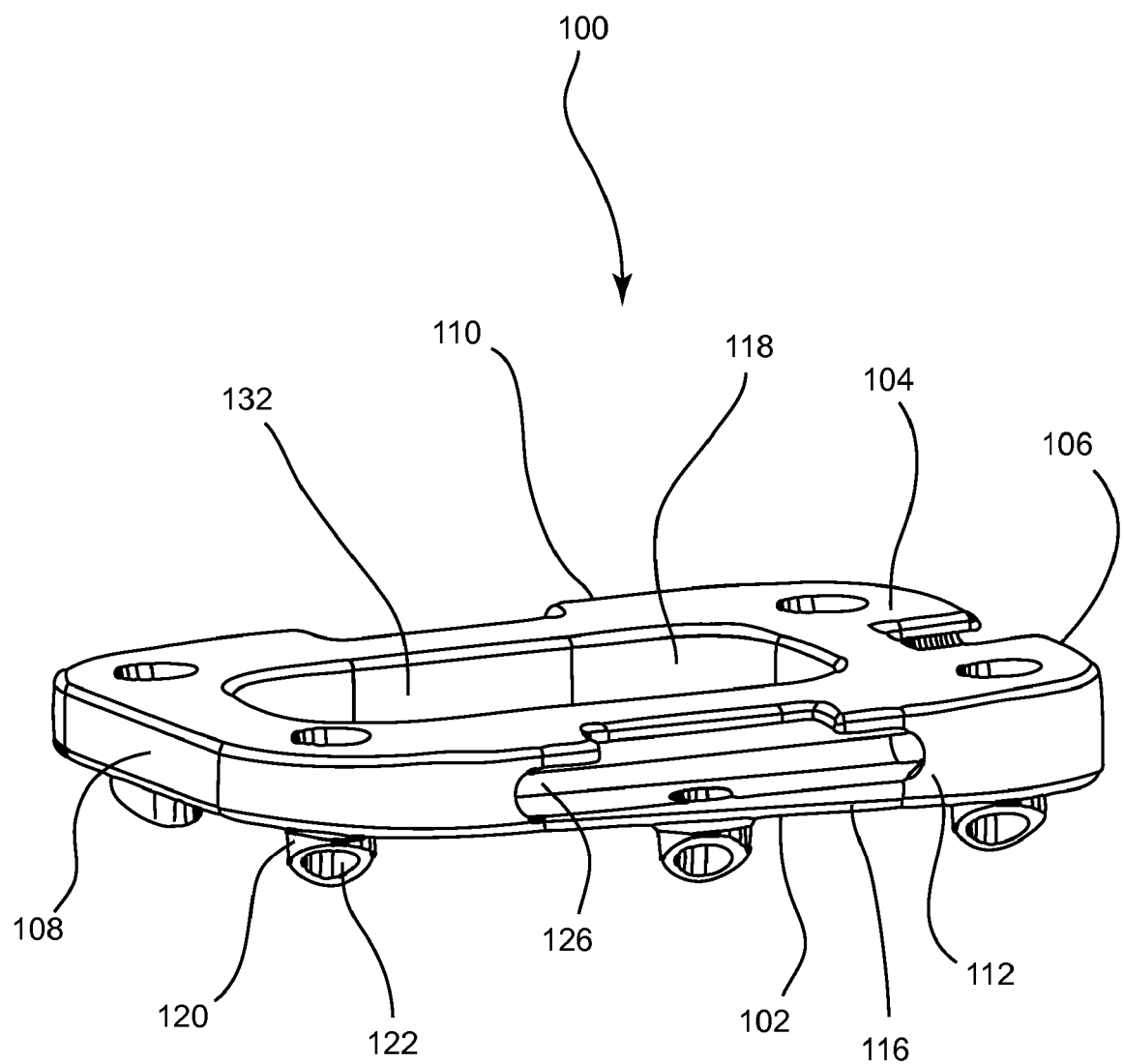
FIG. 4 is a perspective lateral side view of the inferior end plate shown in FIG. 2.

As viewed in FIGS. 3 and 4, the inferior end plate 100 is quadrilateral in form, with rounded corners, and is bilaterally symmetrical. It has a bone-facing side 102, a bearing-facing side 104, an anterior end 106, a posterior end 108, a right end 110 and a left end 112. The end plate is slightly wedge-shaped, with the height of the anterior end 106 slightly greater than the posterior end 108. This is to match the natural lordotic angle of the lumbar vertebrae as closely as possible. In alternative embodiments, it is appreciated that the end plates 100, 200 need not have a quadrilateral configuration but can be square, circular, or have any other polygonal or irregular configuration. Furthermore, it is appreciated that the end plates 100, 200 can be configured at any desired wedge angle or can have substantially parallel top and bottom surfaces.

The inferior end plate 100 has a bone engaging face 114 and a bearing engaging face 116 which are connected by a support member 118. Projecting from the bone engaging face 114 is a plurality of anchoring members in the form of bone engaging spikes 120. Each bone engaging spike 120 is columnar in form and projects perpendicularly in the caudal direction from the bone engaging face 114. The caudal end of each bone engaging spike 120 tapers and terminates in an acute angle. This angled tapering creates a point which facilitates seating the inferior end plate 100 in the adjacent vertebral body 22 during the implantation process; the point will more easily penetrate the vertebral body 22 than would a blunt end.

A hollow grafting channel 122 runs through the center of each bone engaging spike 120. Each grafting channel 122 originates on the bearing engaging face 114, runs through the support member 118, and ends at the pointed termination of the bone engaging spike 120. This hollowed point configuration may be compared to the point of a hypodermic needle, and further facilitates the penetration of the vertebral body 22 by the bone engaging spikes 120. The grafting channels 122 also allow for the growth of bony columns from the vertebral body 22 through the channels, thereby fusing the inferior end plate 100 to the vertebral body 22.

Figure 5:
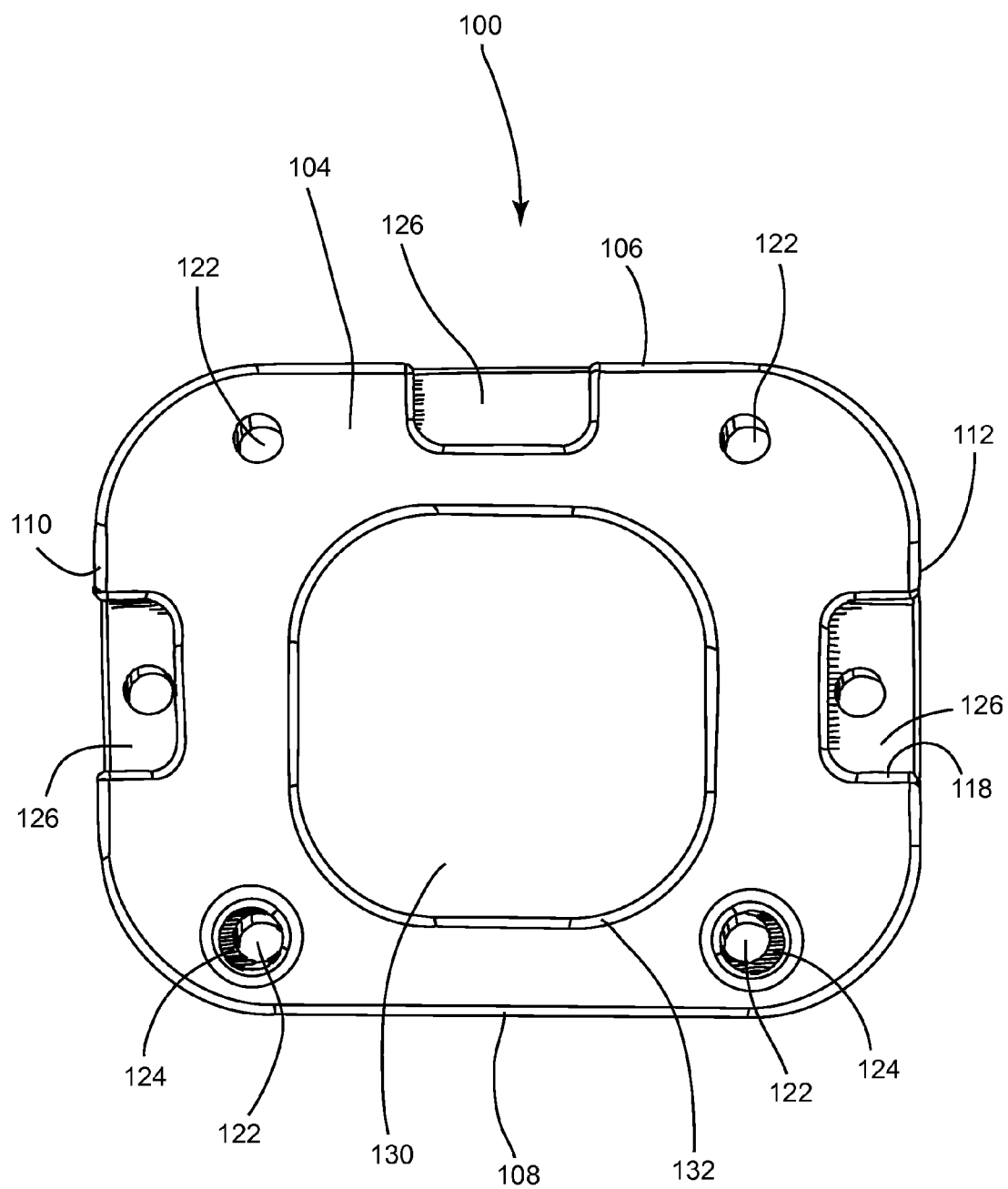
FIG. 5 is a cephalad view of the bearing-facing side of the inferior end plate shown in FIG. 2.

FIG. 5 illustrates the bearing-facing side 104 of the inferior end plate 100. Near the corner formed by the posterior end 108 and the left end 112 is a peg port 124. The peg port 124 is a circular opening originating on the bearing-engaging face 116 and recessed into the support member 118. Partway through the support member 118, the width of the peg port 124 constricts and the port continues as a grafting channel 122, exiting through a bone engaging spike 120 on the bone-facing side 102. A similar peg port 124 is located near the right posterior corner.

Centered on the anterior end 106 of the bearing-facing side 104 is a pocket 126. Similar pockets are centered on the right end 110 and the left end 112. Each pocket 126 is a rectangular segment cut from the edge of the bearing-engaging face 116 and extending caudally into the support member 118. Once the cutaway area is below the bearing-engaging face 116, the slot widens on either lateral side, and deepens perpendicularly into the support member 118, toward the center of the end plate. The pockets 126 are places where implantation instruments (not shown) may grip or otherwise connect with the end plates during the implantation procedure. The number, size, configuration and placement of pockets may vary in other embodiments of the invention.

As seen in FIGS. 3, 4 and 5, a snap port 130 is located on the end plate 100, laterally centered but slightly displaced toward posterior end 108. The snap port 130 is an opening from the bearing-facing side 104 to the bone-facing side 102, circumscribed by a tapered wall 132. The tapered wall 132 angles outward toward the bone-facing side 102, such that the cross-sectional area of the snap port 130 on the bearing-facing side 104 is smaller than the cross-sectional area of the same snap port 130 on the bone-facing side 102.

Figure 6:
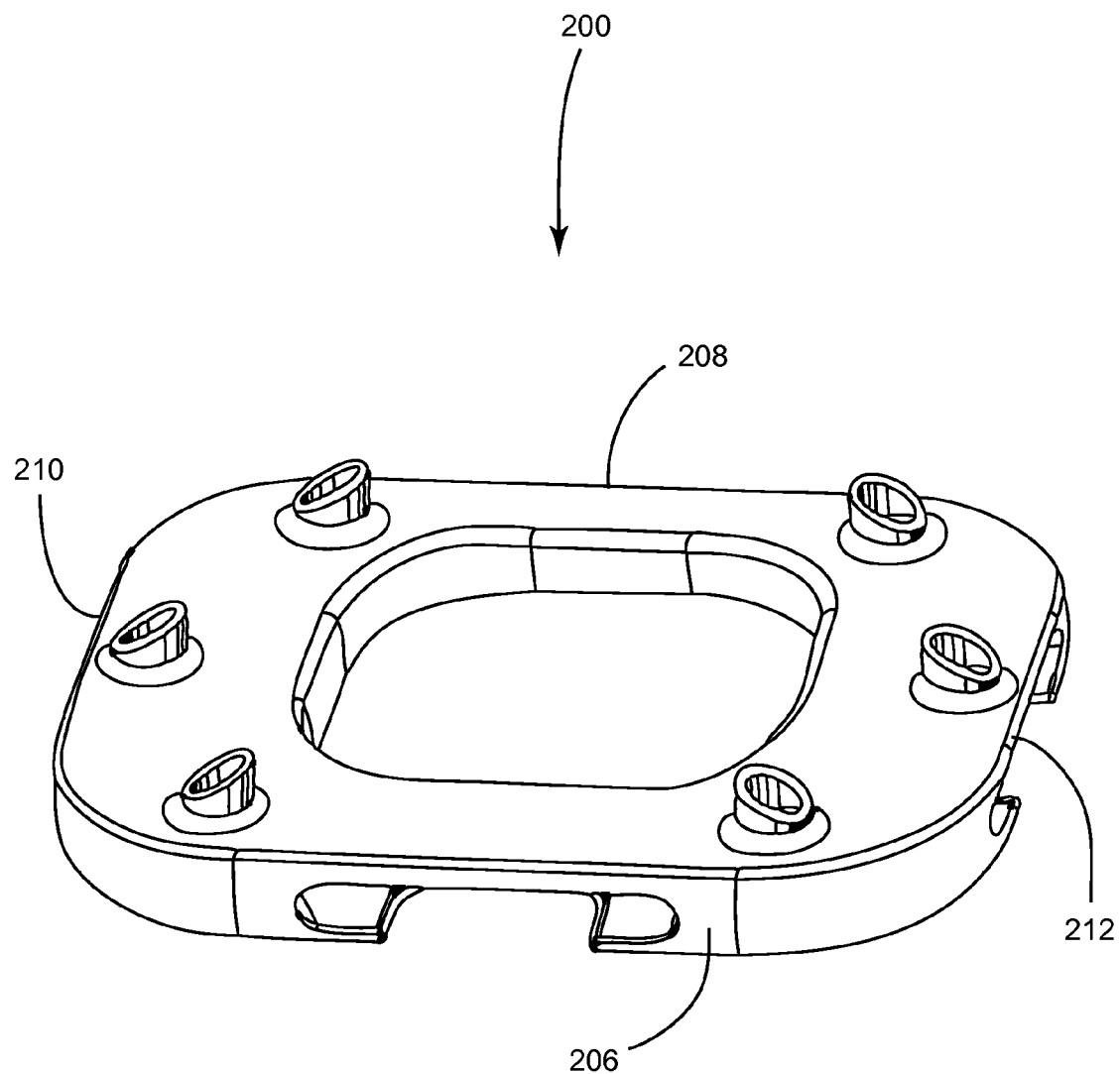
FIG. 6 is a perspective view of the superior end plate shown in FIG. 2.

FIG. 6 is a perspective view of the superior end plate 200. Note that as discussed earlier, the superior end plate 200 is identical to the inferior end plate 100 in every way except in orientation once implanted. However, as illustrated, this does mean that the right end 210 and left end 212 of the superior end plate 200 are reversed from the right end 110 and left end 112 of the inferior end plate 100.

Figure 7:
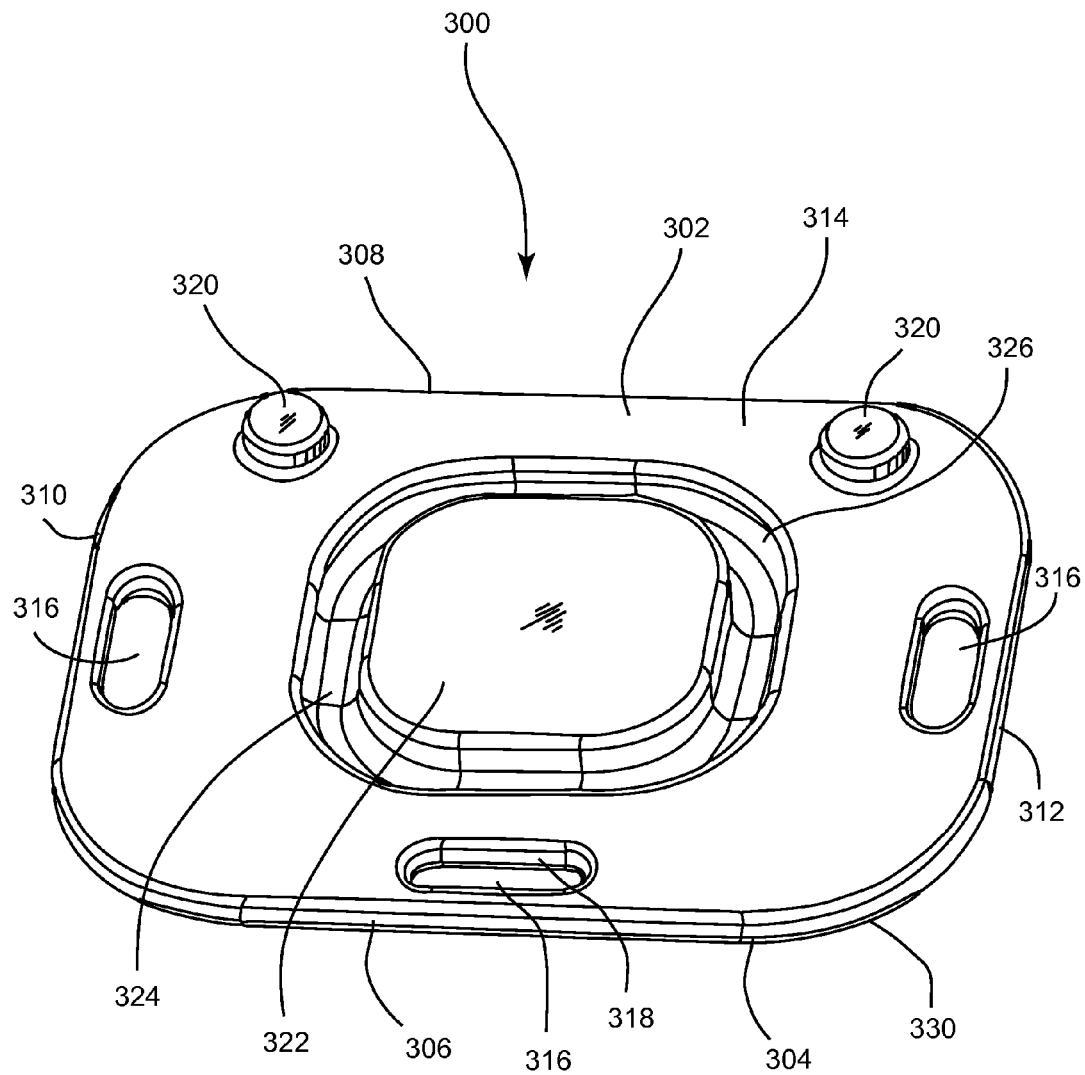
FIG. 7 is a perspective view of the caudal side of the inferior bearing shown in FIG. 2.

Once the end plates 100, 200 are implanted, the bearings 300, 400 are inserted and attached to the end plates. FIG. 7 illustrates the caudal side of the inferior bearing 300. The inferior bearing 300 is of the same approximate quadrilateral shape and dimension as the inferior end plate 100. It has a caudal side 302, a cephalad side 304, an anterior end 306, a posterior end 308, a right end 310 and a left end 312. On the caudal side 302 is an end plate-engaging face 314. Centered along the anterior end 306 is an instrument port 316, which is an opening originating on the end plate engaging face 314, passing through a support member 318, and terminating on an inferior articulation surface 330. Additional instrument ports 316 are centered on the right end 310 and the left end 312. Protruding from the end plate-engaging face 314 near the posterior right and left corners are two pegs 320. The pegs 320 fit into the peg ports 124 shown in FIG. 5, when the inferior bearing 300 is attached to the inferior end plate 100. The fitting of the pegs 320 into the peg ports 124 assist in reducing shear stress on the implant.

Occupying the central area of the inferior bearing 300 is a cap 322, surrounded by a trough 324. The cap is a quadrilateral protrusion from the end plate engaging face 314, and the surface of the cap 322, while parallel to the end plate engaging face 314, is slightly elevated from it. The trough 324 which surrounds the cap is recessed from the end plate engaging face 314 into the support member 318. The outer boundary of the trough is a tapered wall 326. The tapered wall 326 angles inward from the bottom of the trough 324 to the top, such that the cross sectional area of the trough 324 at its deepest point is larger than its cross sectional area where it meets the surface of the end plate engaging face 314.

Figure 8:
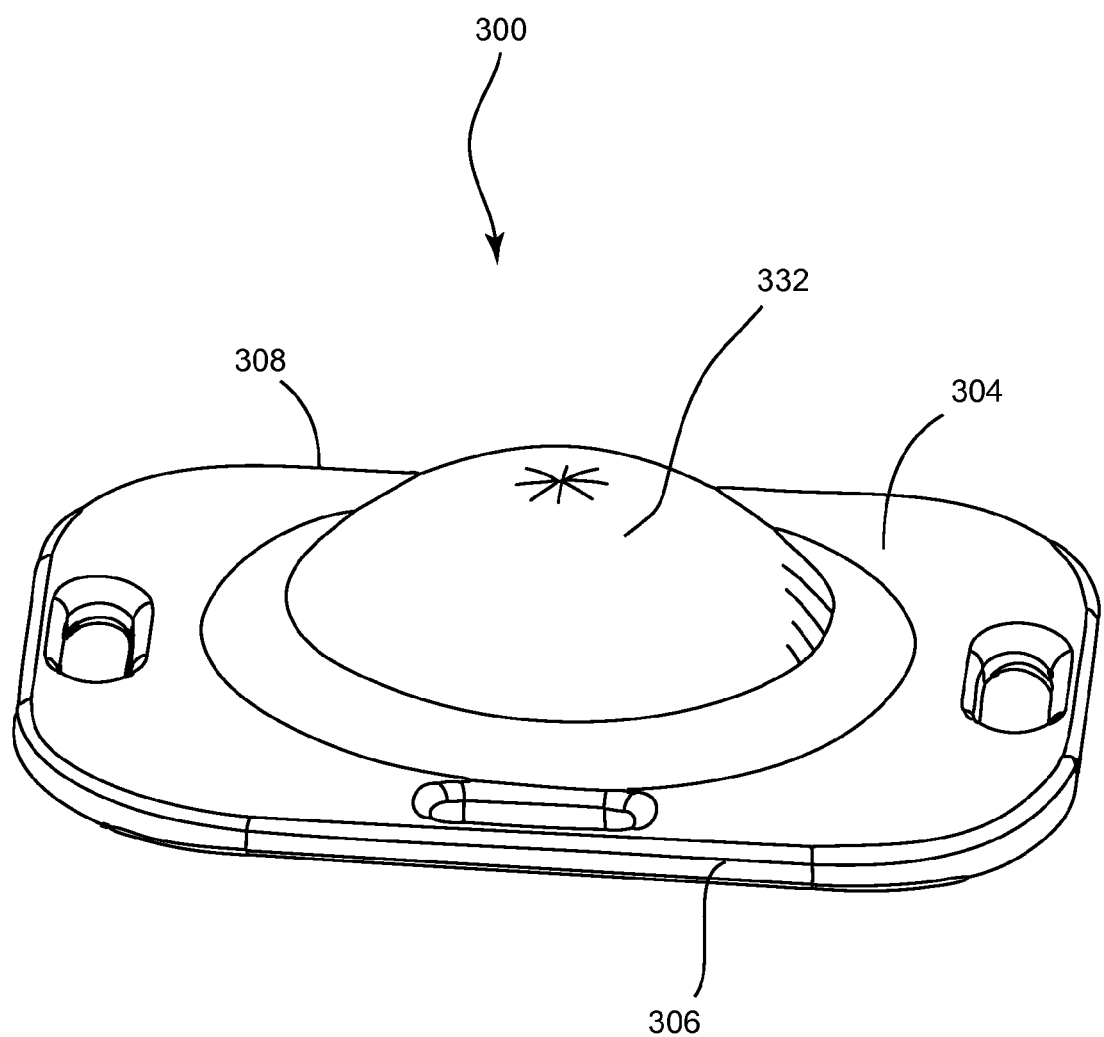
FIG. 8 is a perspective view of the cephalad side of the inferior bearing shown in FIG. 2.

FIG. 8 displays the cephalad side 304 of the inferior bearing 300. The cephalad side has an inferior articulation surface 330 from which arises a rounded dome 332. The dome 332 is centered laterally on the cephalad side 304 of the inferior bearing 300, but is slightly displaced toward the posterior end 308.

Figure 9:
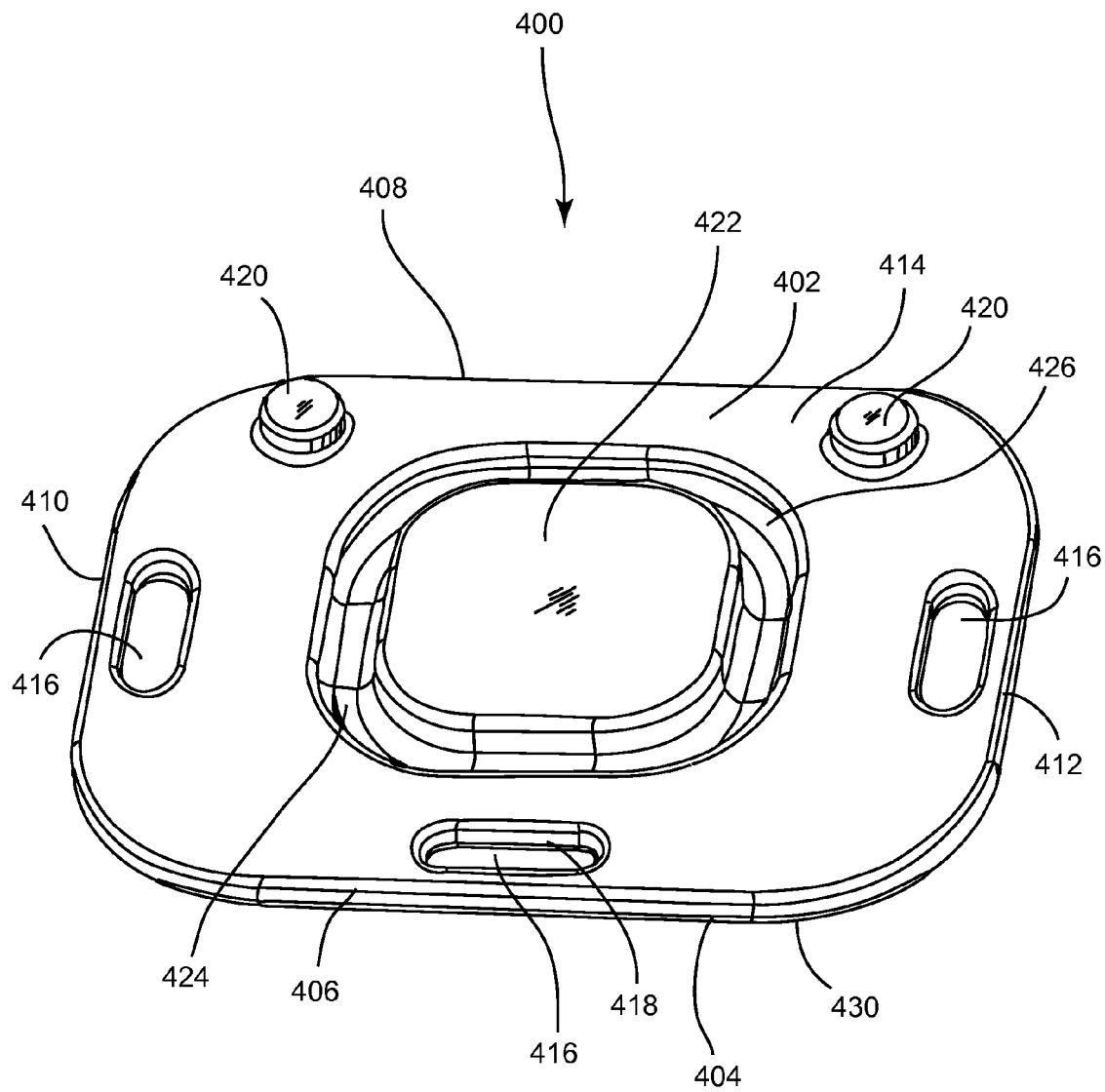
FIG. 9 is a perspective view of the cephalad side of the superior bearing shown in FIG. 2.

FIG. 9 illustrates the cephalad side 402 of the superior bearing 400. It has a cephalad side 402, a caudal side 404, an anterior end 406, a posterior end 408, a right end 410 and a left end 412. On the cephalad side 404 is an end plate-engaging face 414. Centered along the anterior end 406 is an instrument port 416, which is an opening originating on the end plate engaging face 414, passing through a support member 418, and terminating on a superior articulation surface 430. Additional instrument ports 416 are centered on the right end 410 and the left end 412. Protruding from the end plate-engaging face 414 near the posterior right and left corners are two pegs 420. The pegs 420 fit into the peg ports 224 shown in FIG. 6, when the inferior bearing 400 is attached to the superior end plate 200. The fitting of the pegs 420 into the peg ports 224 assist in reducing shear stress on the implant.

Occupying the central area of the superior bearing 400 is a cap 422, surrounded by a trough 424. The cap 422 is a flat-topped protrusion from the end plate engaging face 414, and the surface of the cap 422, while parallel to the end plate engaging face 414, is slightly elevated from it. The trough 424 which surrounds the cap is recessed from the end plate engaging face 414 into the support member 418. The outer boundary of the trough is a tapered wall 426. The tapered wall 426 angles inward from the bottom of the trough 424 to the top, such that the cross sectional area of the trough 424 at its deepest point is larger than its cross sectional area where it meets the surface of the end plate engaging face 414.

Figure 10:
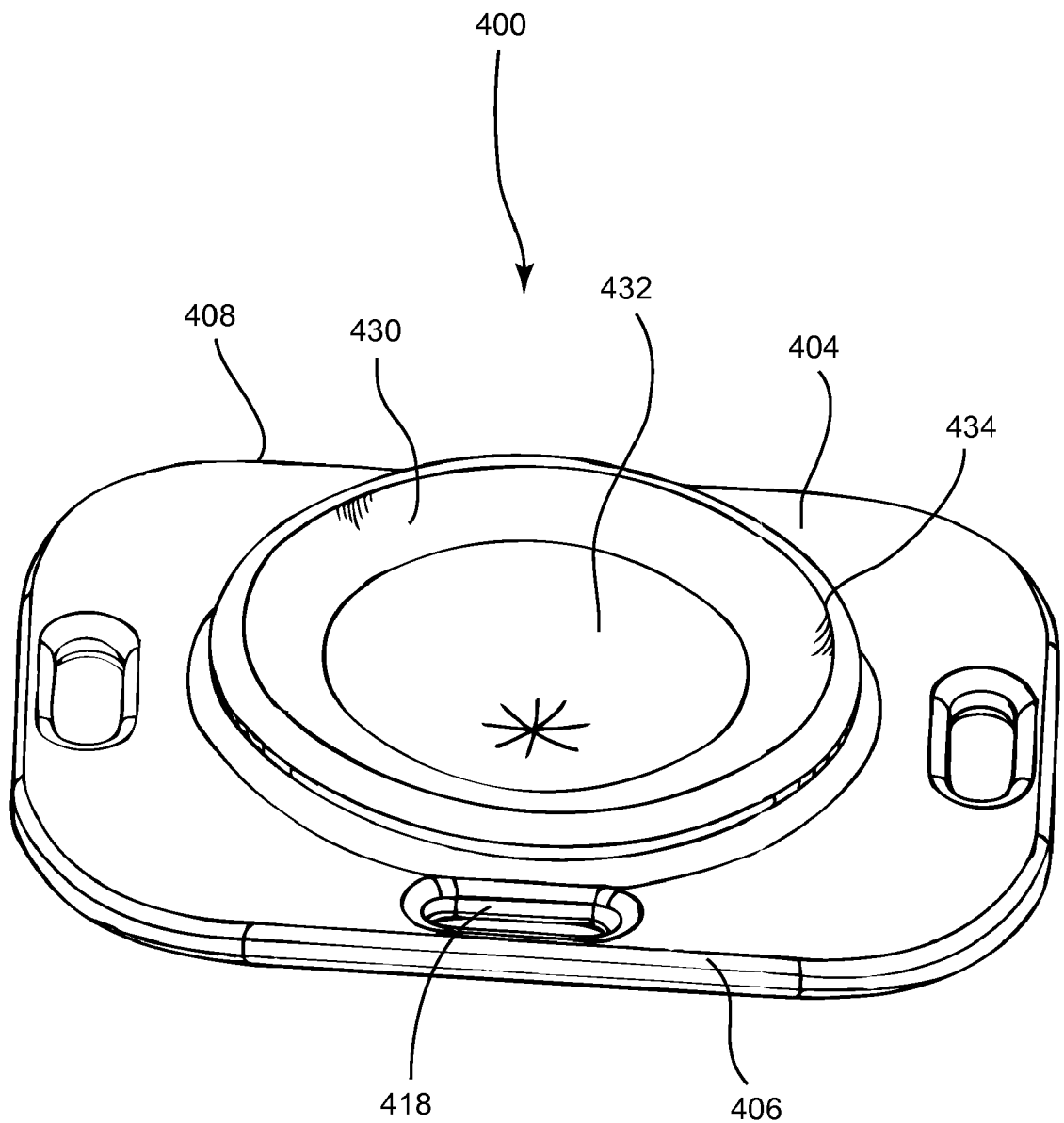
FIG. 10 is a perspective view of the caudal side of the superior bearing shown in FIG. 2.

The caudal side 404 of the superior bearing 400 is illustrated in FIG. 10. A rounded cup 432 is recessed into the support member 418 of the caudal side 404. The cup 432 is centered laterally on the caudal side 404, but is slightly displaced toward the posterior end 408. A ridge 434 encircles the cup 432. The ridge is raised substantially from the support member 418. A smooth superior articulation surface 430 overlays the ridge 434 and the cup 432 such that where they meet, there is no discernable transition between the two features.

Figure 11:
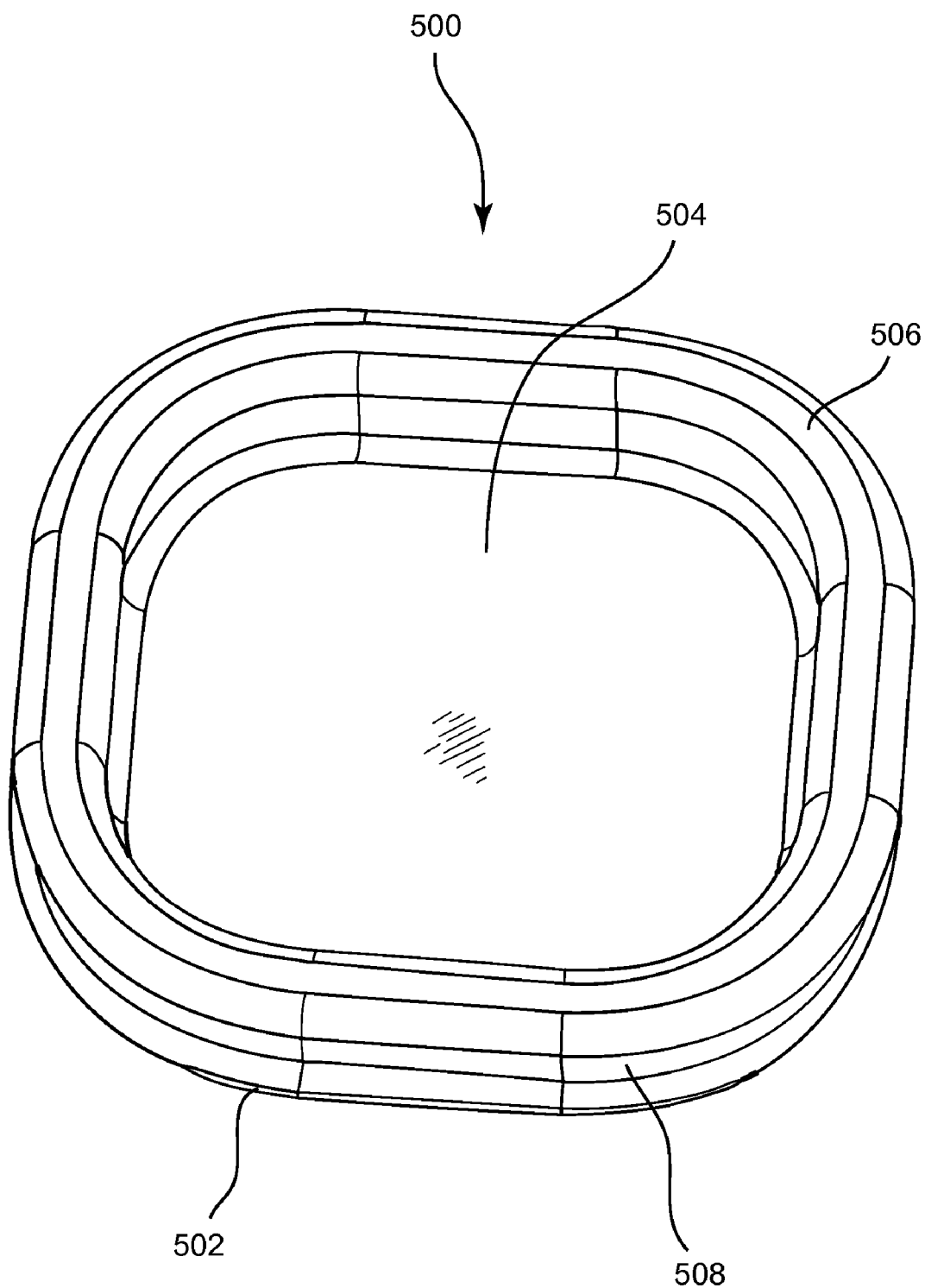
FIG. 11 is a perspective view of the bearing-facing side of the snap shown in FIG. 2.
Figure 12:
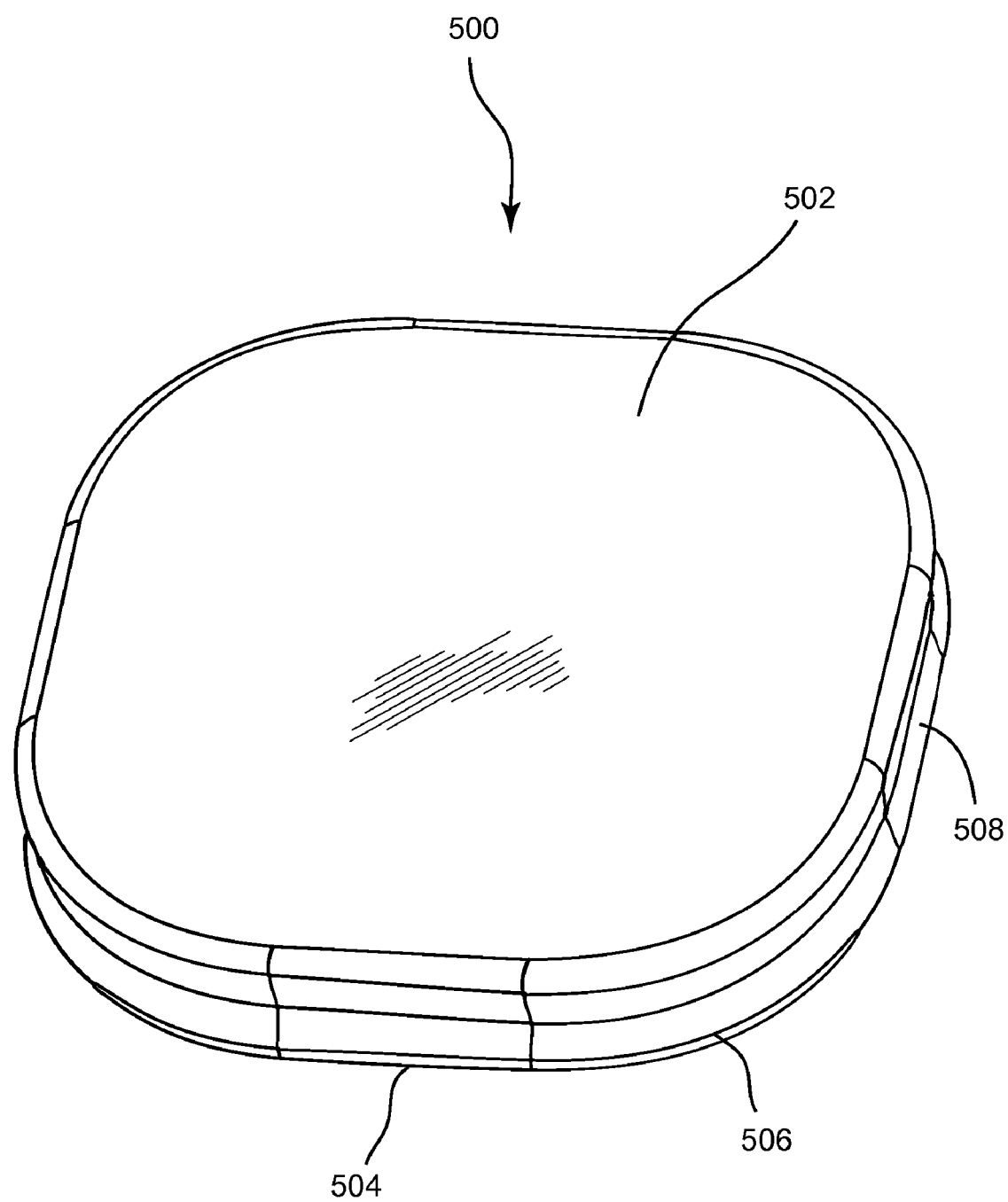
FIG. 12 is a perspective view of the end plate-facing side of the snap shown in FIG. 2.
Figure 13:
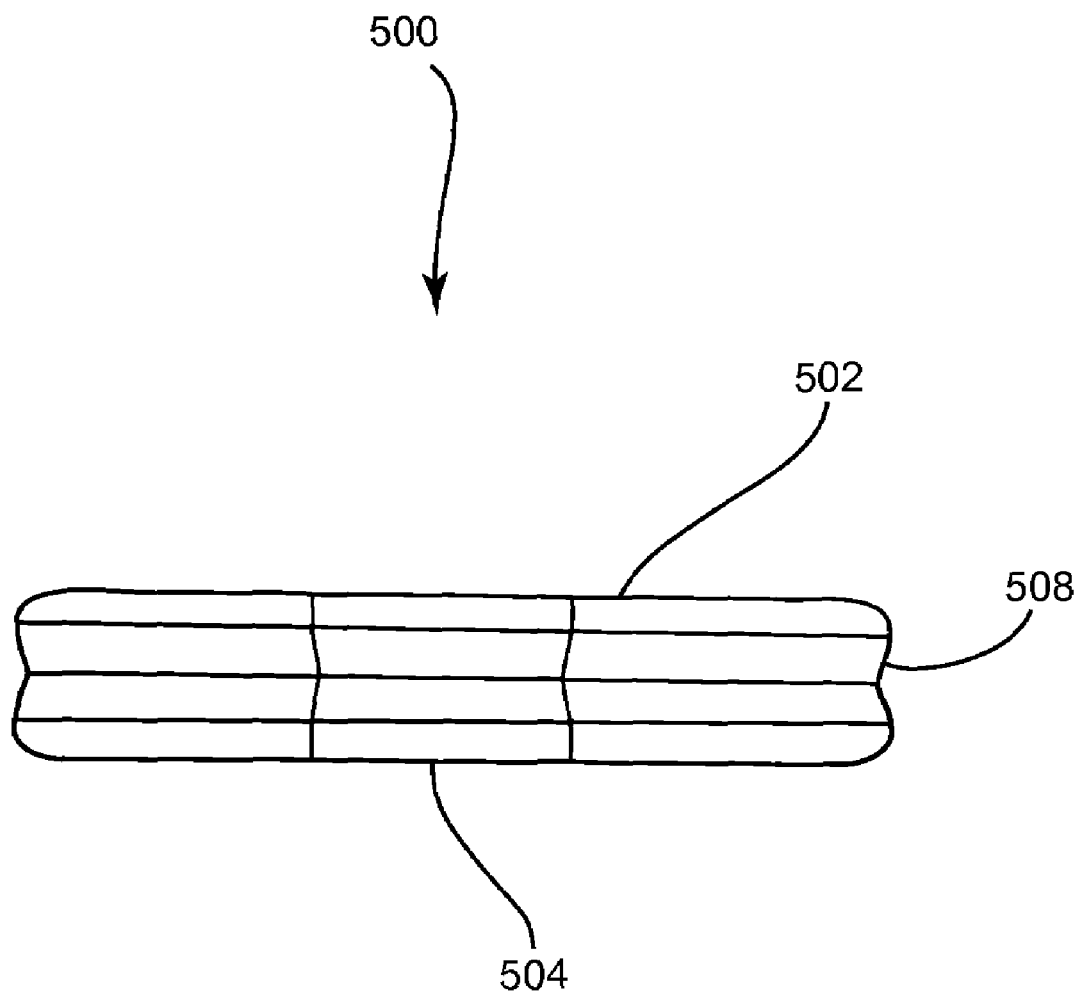
FIG. 13 is a lateral view of the snap shown in FIG. 2.

As seen in FIG. 2, the snap 500 serves as the connector between the inferior end plate 100 and the inferior bearing 300, and between the superior end plate 200 and the superior bearing 400. FIGS. 11, 12 and 13 illustrate the snap 500 alone. In this embodiment of the invention, the snap 500 is quadrilateral and generally dish-like in form, with a bone-facing side 502 which is a substantially flat plane, and a bearing facing side 504 which is a flat plane circumscribed by a raised rim 506. It is appreciated that in alternative embodiments of the invention, the snap feature may be quadrilateral, circular or any other shape or configuration. The outer edge of the rim 506 is formed by a dual-tapered wall 508. As seen best in FIG. 13, the dual-tapered wall 508 is equally wide at the bone-facing side 502 and at the bearing-facing side 504, but constricts at the midpoint between the two sides 502, 504.

FIG. 2 best illustrates how all the components of the implant 50 fit together. During or after manufacture, but before the implantation procedure, one snap 500 is fitted over the cap 322 of the inferior bearing 300, and a second snap 500 is fitted over the cap 422 of the superior bearing 400. As the rim 506 of the snap 500 is pressed into the trough 324 of the inferior bearing 300, the dual-tapered wall 508 compresses to pass into the trough 324, then expands out into place such that the dual-tapered wall 508 fits against the tapered wall 326 of the trough. Because the widest part of the dual-tapered wall 508 is wider than the opening of the trough 324, the snap 500 is locked into place, and can only be removed from the inferior bearing 300 with significant force. The second snap 500 is attached to the superior bearing 400 in the same manner.

The inferior end plate 100 is implanted in the vertebral body 22, and the superior end plate 200 is implanted in the vertebral body 42. The inferior bearing 300 is pressed into place in the inferior end plate 100. The bone-facing side 502 of the snap 500, now protruding from the caudal side 302 of the inferior bearing 300, is pressed into the snap port 130 of the inferior end plate 100. As the bone-facing side 502 of the snap 500 is pressed into the snap port 130, the dual-tapered wall 526 compresses to pass into the snap port 130, then expands out into place such that the dual-tapered wall 526 fits against the tapered wall 132 of the inferior end plate 132. Because the widest part of the dual-tapered wall 526 is wider than the opening of the snap port 130, the snap 500 is locked into place, and can only be removed from the inferior end plate 100 with significant force.

The superior bearing 400 and its snap 500 are attached to the superior end plate 200, in the same manner as described above for the inferior end plate 100 and bearing 300. Then the inferior articulation surface 330 is allowed to contact the superior articulation surface 430. Although in this description, the inferior bearing and its snap were attached first, followed by the superior bearing and its snap, it is appreciated that the bearings may be attached in either order. It is also appreciated that should there be any subsequent procedure for replacement or adjustment of any of the end plates, bearings or snaps, such procedure may be carried out from any one of the three approaches; anterior, left lateral or right lateral.

Figure 14:
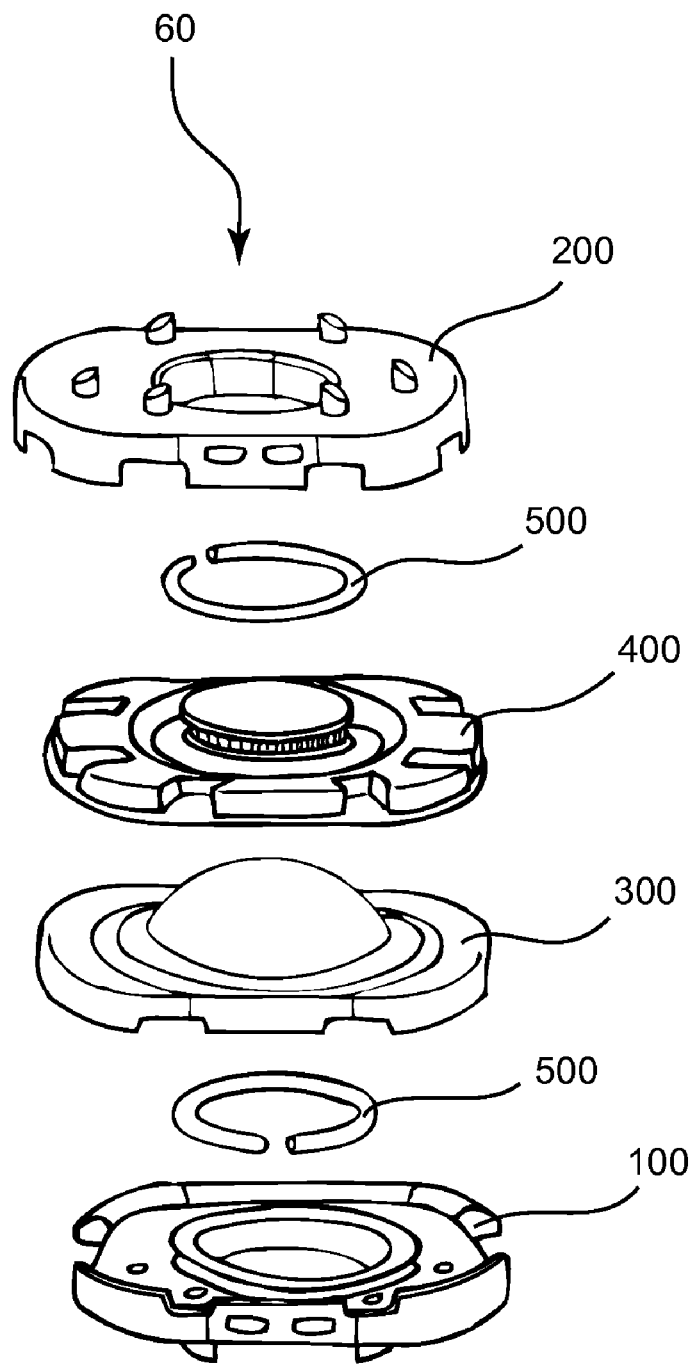
FIG. 14 is a perspective view of an alternative embodiment of a total disc implant, in a disassembled state.

Other embodiments of the invention can provide the same function while employing alternate snap connections. FIG. 14 depicts a disassembled total disc implant 60, which employs an alternate snap feature to lock the bearings to the end plates. In this embodiment, the inferior bearing 300 is connected to the inferior end plate 100 via a ring-shaped snap 500. Similarly, the superior bearing 400 is connected to the superior end plate 200 by the same ring-shaped snap 500. The mechanism by which the snap locks the bearings to the end plates is equivalent to the snap feature described in the first embodiment; in both embodiments the snap feature compresses to pass through a constrictive feature, and then expands out to lock the components in place.

Figure 15:
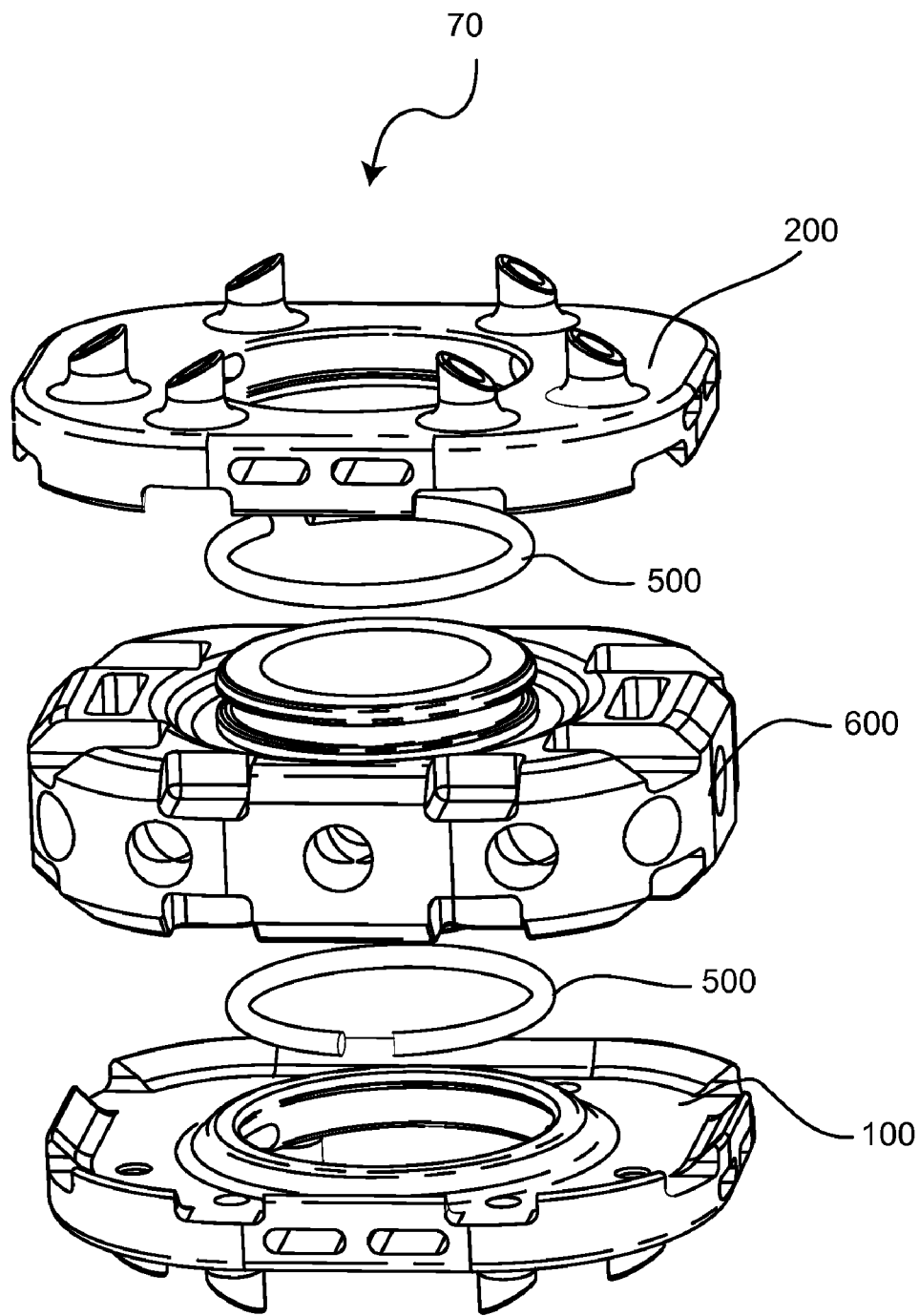
FIG. 15 is a perspective view of an interbody disc fusion implant, in a disassembled state.

If fusion of the vertebrae is required, an embodiment of the invention including a fusion block may be implemented. FIG. 15 depicts an interbody disc fusion implant 70, in a disassembled state. In this embodiment, the implant consists of an inferior end plate 100, a superior end plate 200, two ring-shaped snaps 500 and a fusion cage 600. The interbody disc fusion implant 70 may be implanted from an anterior approach, a right lateral approach, or a left lateral approach. It may be implanted as part of the initial implantation procedure, or it may replace inferior and superior bearings, upon their removal.

Figure 16:
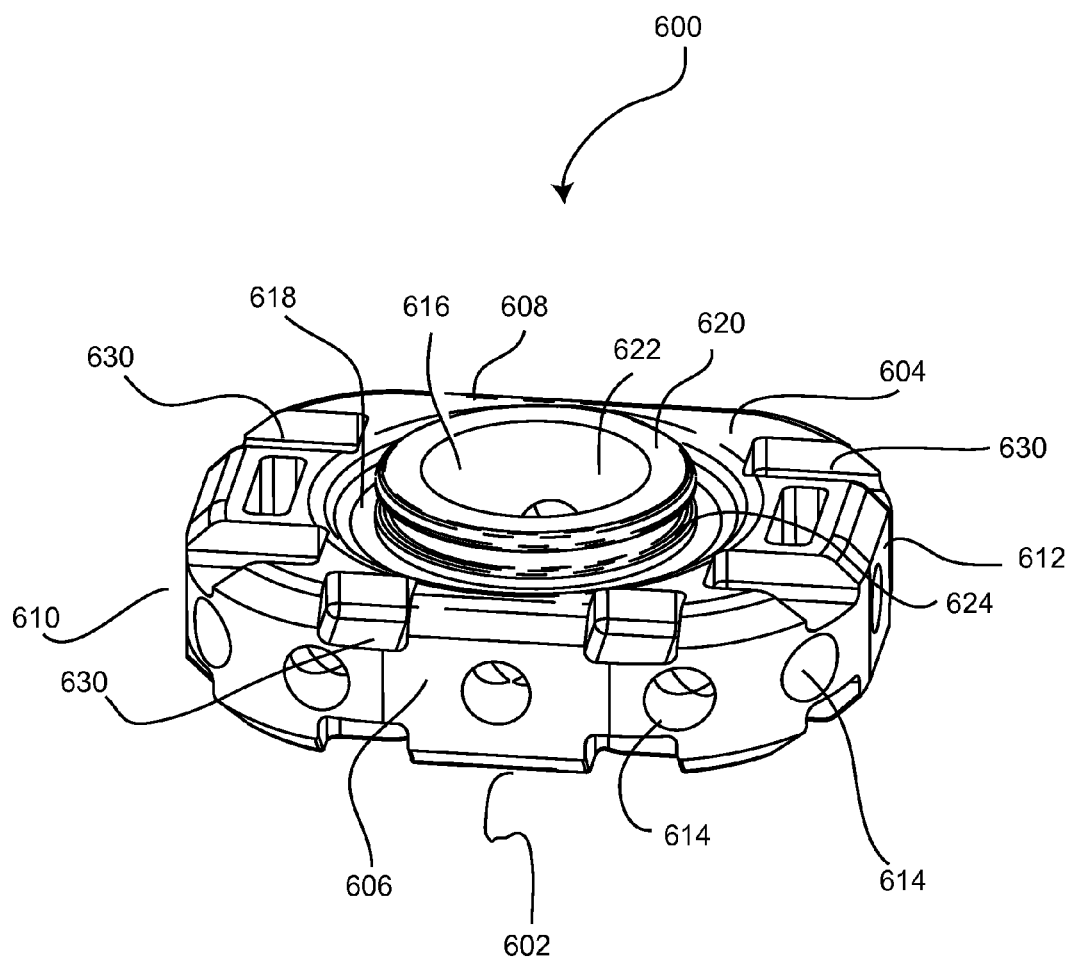
FIG. 16 is a perspective view of the fusion cage shown in FIG. 15.

FIG. 16 illustrates the fusion cage 600. In this embodiment of the invention, the fusion cage 600 is quadrilateral and box-like in shape. It has a caudal side 602, a cephalad side 604, an anterior end 606, a posterior end 608, a right end 610 and a left end 612. It is symmetrical such that the right and left ends 610, 612 are mirror images of one another and the caudal and cephalad sides 602, 604 are also mirror images. A plurality of notches 630, designed for gripping by implantation instruments (not shown) are at the edges of the caudal and cephalad sides 602, 604.

A plurality of grafting holes 614 perforates each end of the fusion cage. Before, during or after positioning of the end plates between the vertebral bodies, the fusion cage 600 is at least partially packed with an osteogenic substance. In this application, "osteogenic substance" is broadly intended to include natural bone, such as autogenous bone graft or bone allograft, synthetic bone, growth factors and cytokines (including bone morphogenic proteins), and/or combinations thereof. After implantation, growth of bone material through the grafting holes will assist in the fusion of the fusion cage and end plates to the vertebrae.

A larger grafting port 616 is centered on the fusion block, with its openings on the caudal and cephalad sides. Recessed into the surface of the fusion block 600 and circumscribing the grafting port 616, is a trough 618. Around each opening of the grafting port, but to the inside of the trough 618, is a raised rim 620. The raised rim 620 protrudes from surface of the fusion block 600. The inner wall 622 of the raised rim 620 is smooth and is a continuous part of the grafting port 616. The outer wall 624 of the raised rim 620 constricts between the top of the rim and where it joins the trough 618. This constriction is designed to hold the snap ring 500, seen in FIG. 15.

Figure 17:
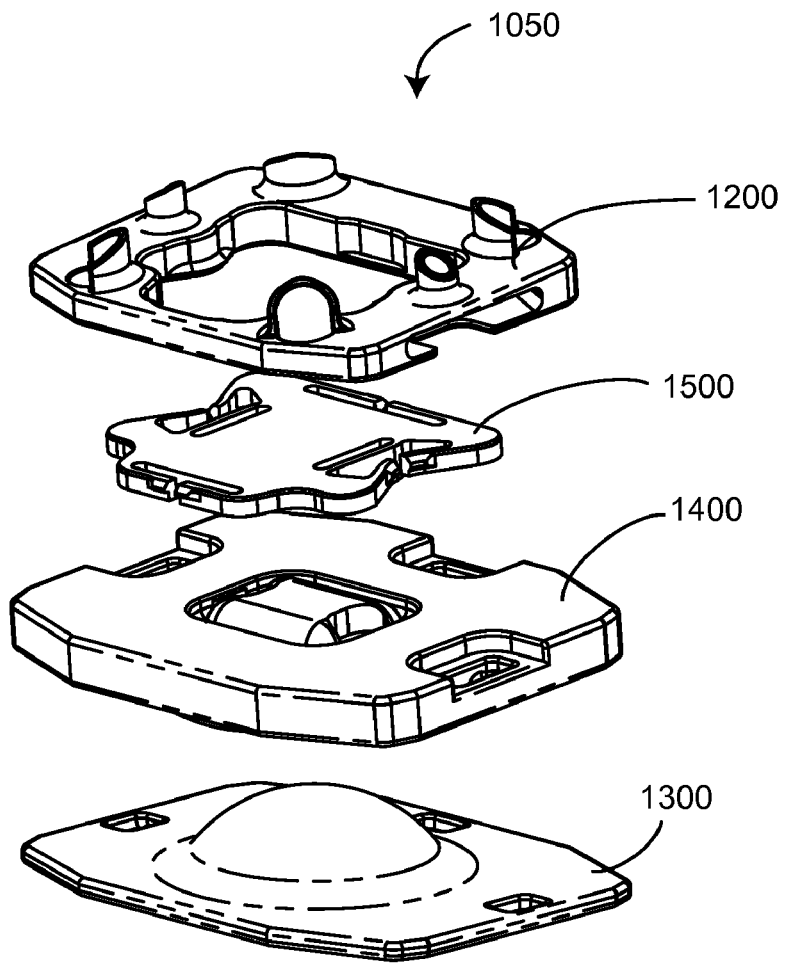
FIG. 17 is a perspective view of another alternative embodiment of a total disc implant, in a disassembled state.
Figure 17:
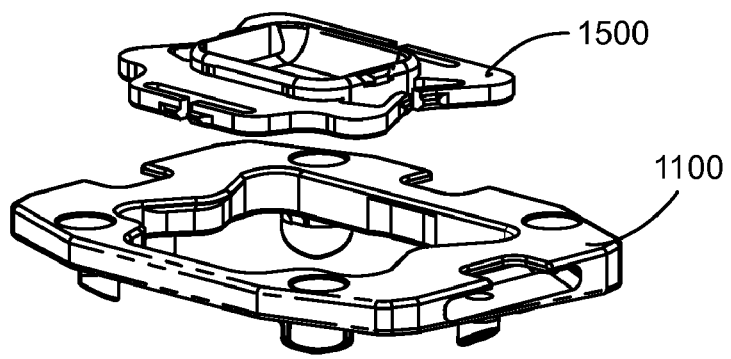

Referring to FIG. 17, an alternative embodiment of a total disk implant is shown. The implant 1050 comprises an inferior end plate 1100, a superior end plate 1200, an inferior bearing 1300, a superior bearing 1400, and two snap fasteners 1500. As with the implant 50, the implant 1050 is designed for placement between spinal vertebrae to replace degenerated intervertebral disk material. Methods for placement, assembly and implantation of the implant 1050 are the same as those described for the implant 50.

Figure 18:
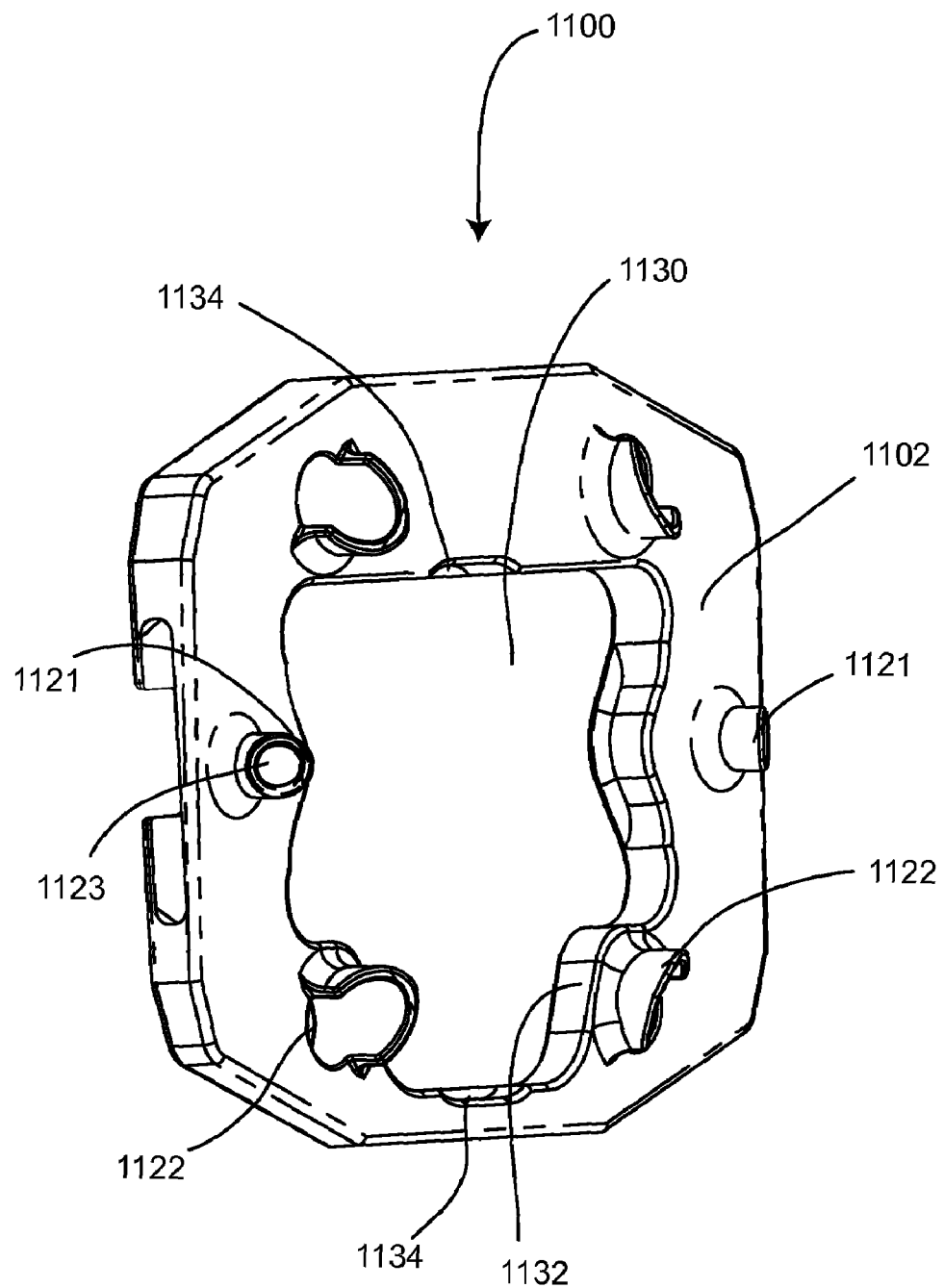
FIG. 18 is a perspective view of a bone-facing side of the inferior endplate shown in FIG. 17.

Referring to FIG. 18, an enlarged view of a bone-facing side of the end plate 1100 is shown. The end plates 1100, 1200 are identical to one another, differing only in their orientation as they are placed between the vertebral bodies. End plate 1100 will be described in detail, but it is appreciated that the same description applies to the end plate 1200. The end plate 1100 has a bone-facing side 1102, and a bearing-facing side 1104. An irregularly shaped snap port 1130 occupies the center of the end plate 1100, creating an opening from the bone-facing side 1102 to the bearing-facing side 1104. A plurality of bone-engaging spikes 1120 are located on the bone-facing side 1102, each adjacent to a grafting channel 1122. Each bone-engaging spike 1120 is of a crescent shape, protruding from the bone-facing side 1102 and terminating with an acute edge. Several small diameter bone-engaging spikes 1121, with small grafting channels 1123 are interspersed with the bone-engaging spikes 1120 and grafting channels 1122.

The large size of the grafting channels 1122 creates favorable conditions for bone ingrowth once the implant 1150 is in place. Also, the crescent shapes of the bone-engaging spikes 1120 allow for good engagement with the vertebral body, but without requiring an excessive amount of force to press into place. The spikes 1122, 1121 also provide shear resistance once the end plate 1100 is implanted in the vertebral body.

The snap port 1130 occupies much of the surface area of the end plate 1100. The large opening size of the snap port 1130 maximizes space available for bone ingrowth. The irregular shape of the snap port 1130 allows more contact area for the snap connection, and offers more torsional resistance than a regularly shaped, round port. The snap port 1130 is encircled by a wall 1132. At several points on the wall 1132, a recess 1134 is indented into the wall 1134.

Figure 19:
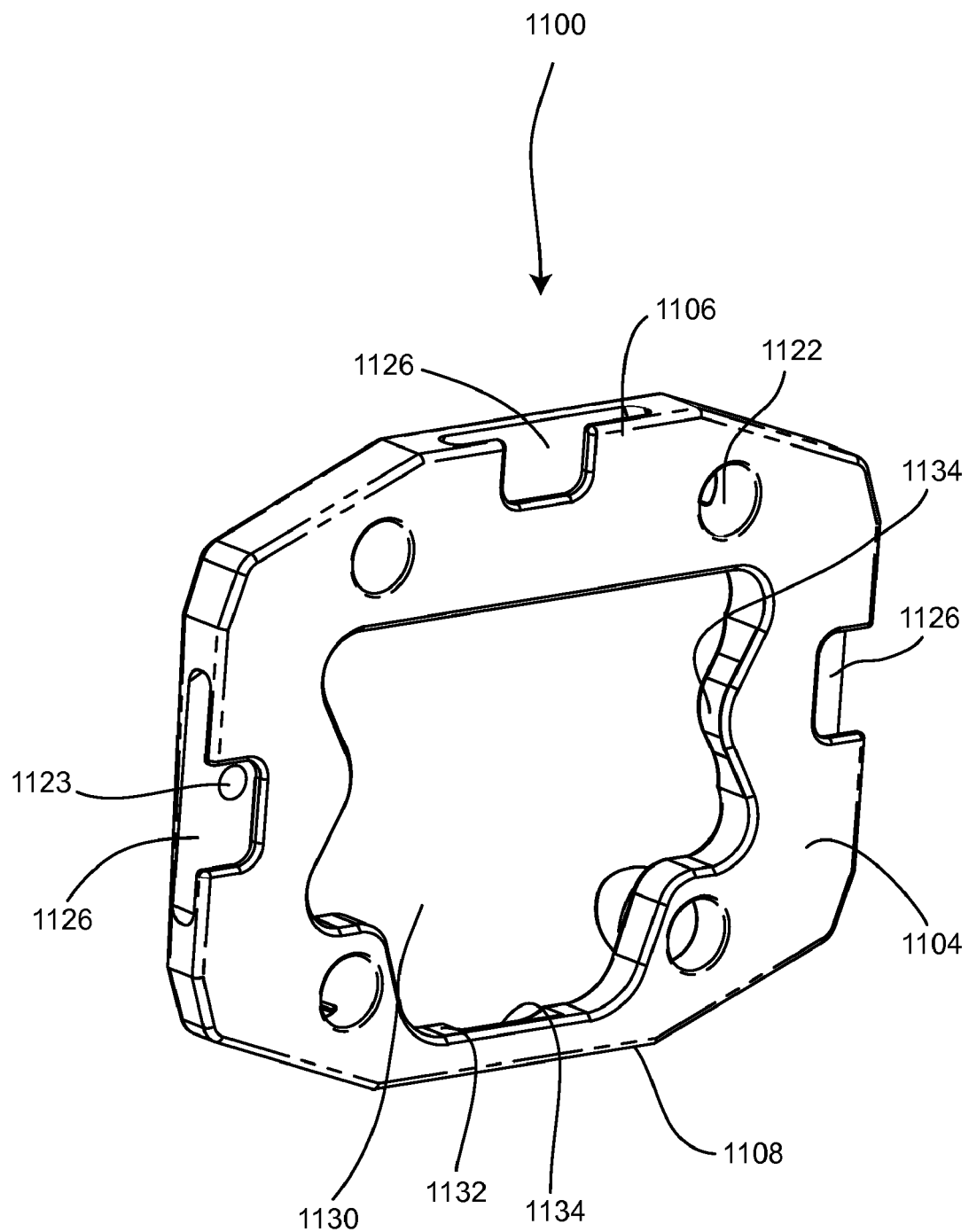
FIG. 19 is a perspective view of a bearing-facing side of the inferior endplate shown in FIG. 17.

Referring to FIG. 19, an enlarged view of the bearing-facing side 1104 of the end plate 1100 is shown. The end plate 1100 has an anterior end 1106 and a posterior end 1108. The grafting channels 1122, 1123 open out on the bearing facing side 1104, as does the snap port 1130. Three pockets 1126 are indented into sides of the end plate 1100, on the anterior end 1106 and the two lateral sides. The pockets 1126 are shaped to engage with the instruments used to insert the end plate 11100.

Figure 20:
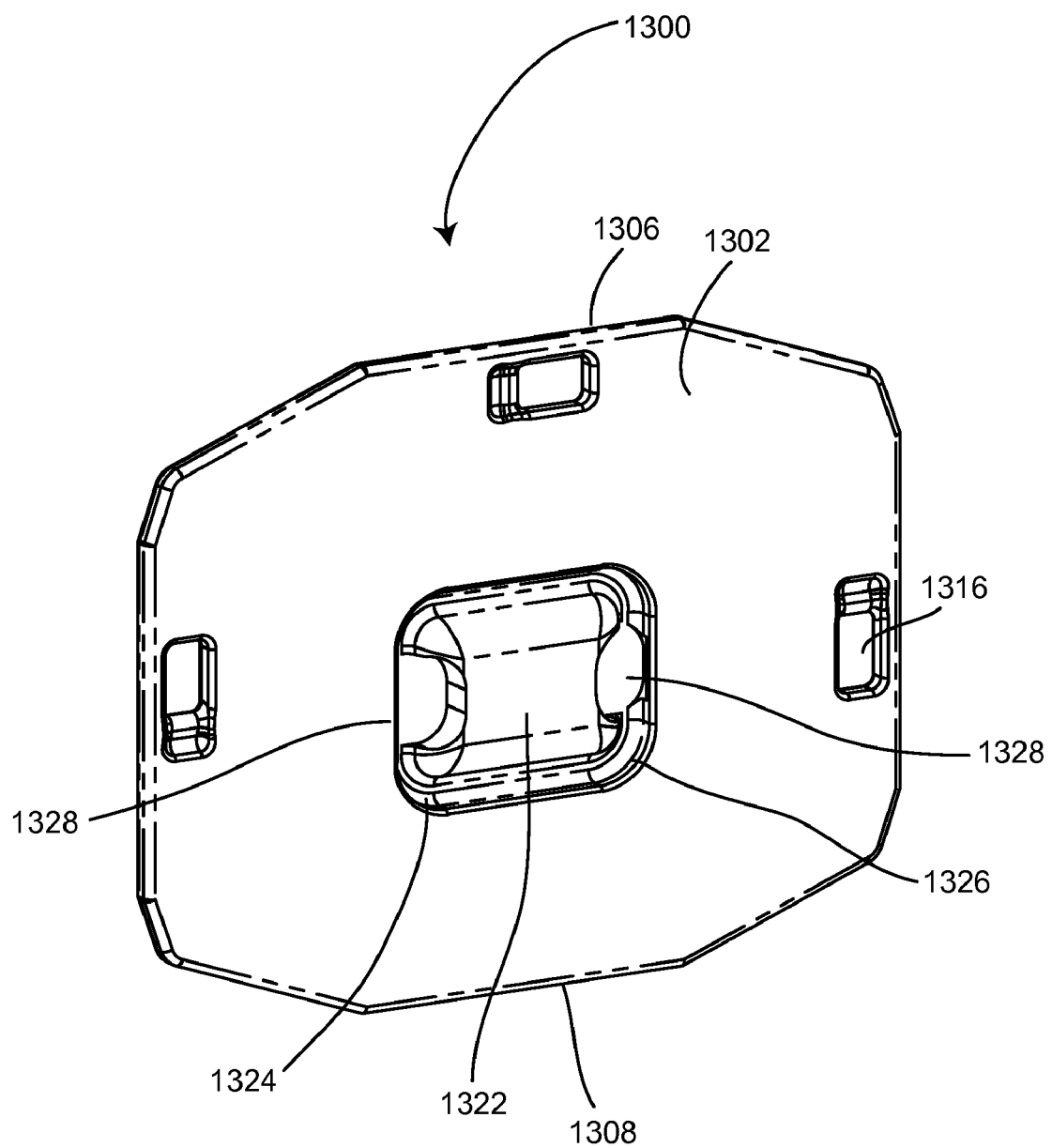
FIG. 20 is a perspective view of a caudal side of the inferior bearing shown in FIG. 17.

Referring to FIG. 20, a caudal side of the inferior bearing 1300 is shown. The inferior bearing 1300 has a caudal side 1302, a cephalad side 1304, an anterior end 1306 and a posterior end 1308. Three instrument ports 1316 perforate the inferior bearing 1300, one on the anterior end 1306 and one on each lateral side. A rounded cap 1322 protrudes from the center of the caudal side 1302, and is surrounded by a trough 1324. The trough 1324 is surrounded by a wall 1326. Indented into each lateral side of the wall 1326 is a long recess 1328.

Figure 21:
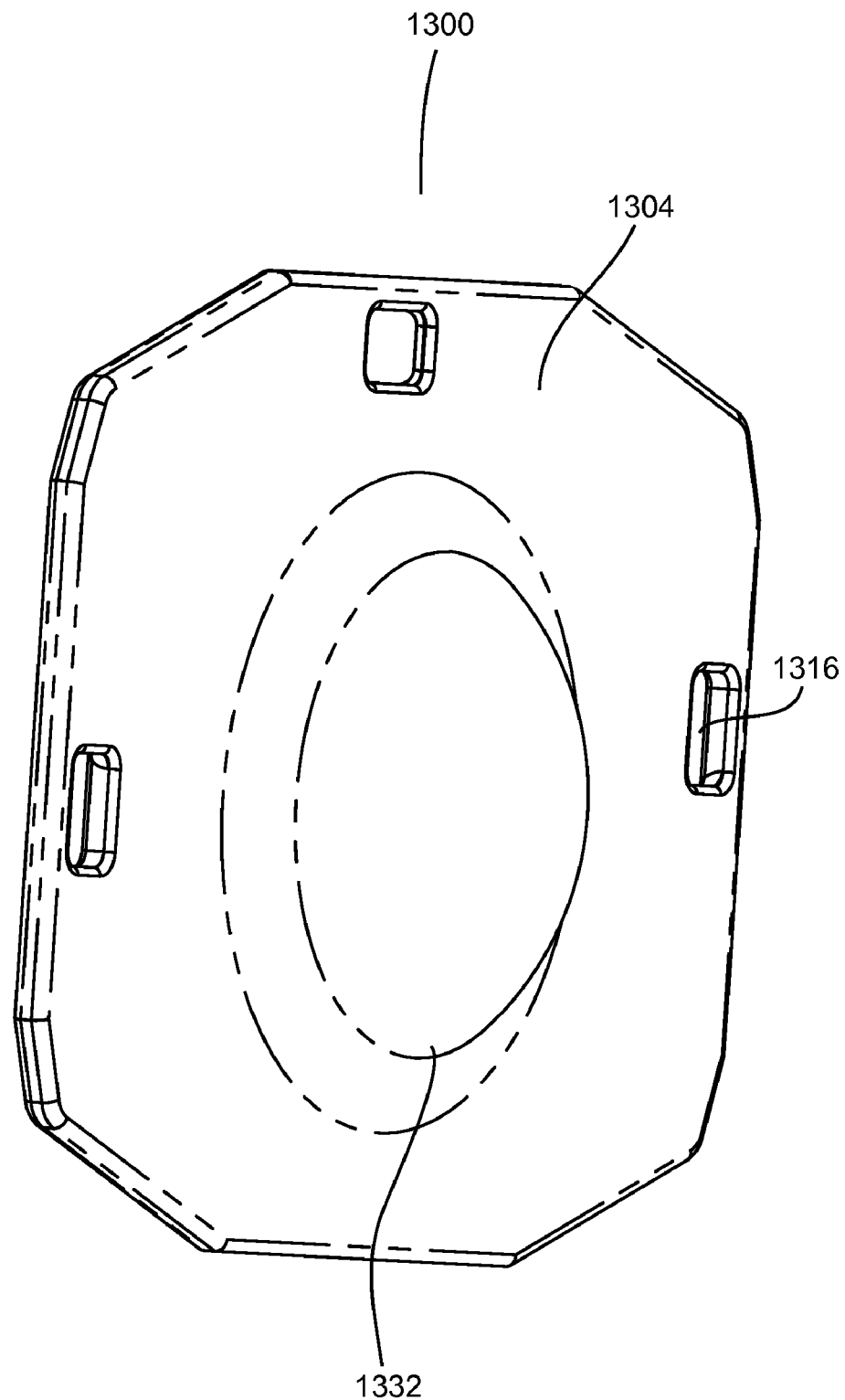
FIG. 21 is a perspective view of a cephalad side of the inferior bearing shown in FIG. 17.

Referring to FIG. 21, the cephalad side 1304 of the inferior bearing 1300 is shown. The three instrument ports 1316 open out on the cephalad side 1304. A round dome 1332 rises from the surface of the cephalad side 1304.

Figure 22:
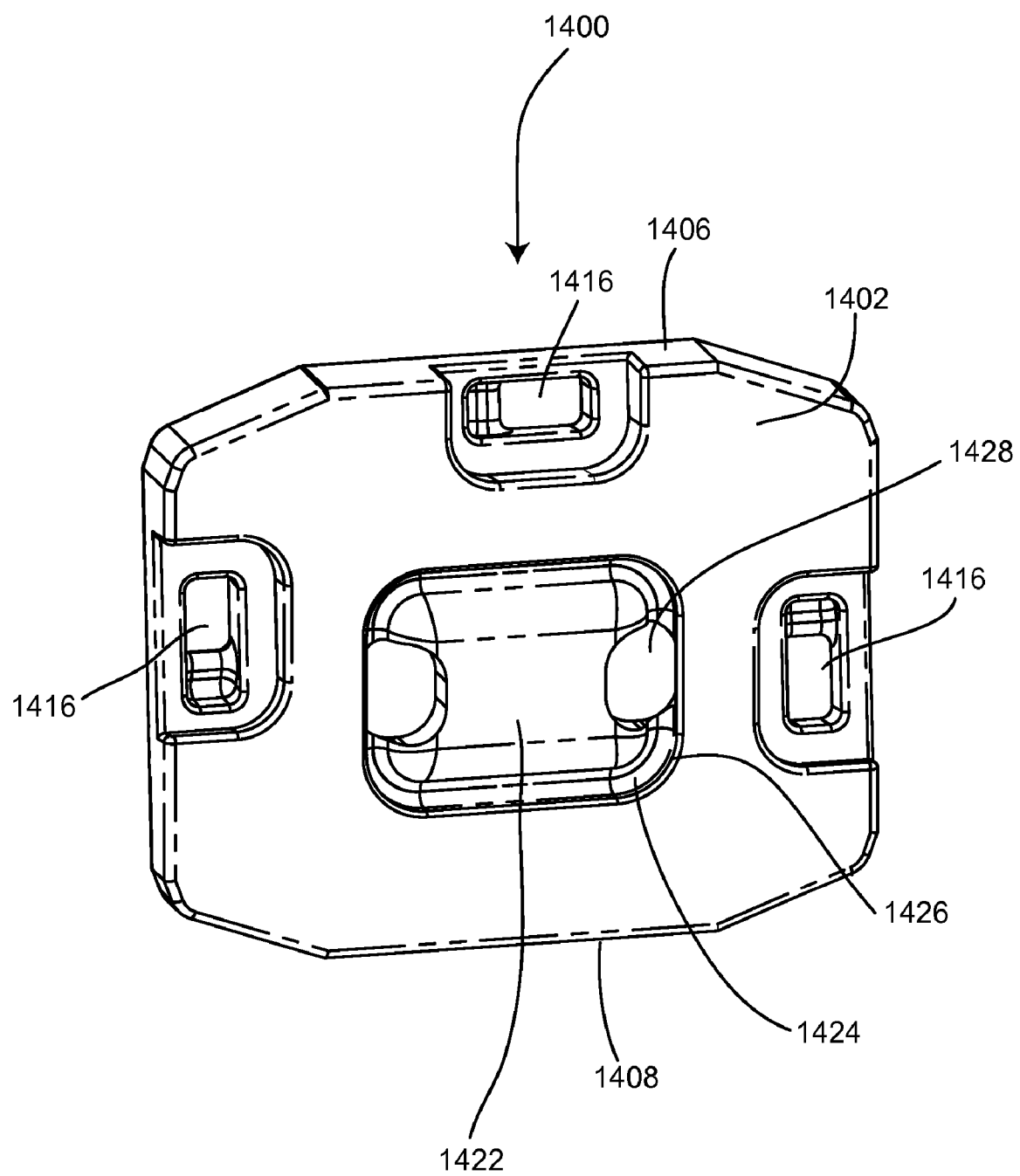
FIG. 22 is a perspective view of a cephalad side of the superior bearing shown in FIG. 17.

Referring to FIG. 22, a cephalad side of the superior bearing 1400 is shown. The superior bearing 1400 has a cephalad side 1402, a caudal side 1404, an anterior end 1406, and a posterior end 1408. Three instrument ports 1416 perforate the inferior bearing 1400, one on the anterior end 1406 and one on each lateral side. A rounded cap 1422 protrudes from the center of the caudal side 1402, and is surrounded by a trough 1424. The trough 1424 is surrounded by a wall 1426. Indented into each lateral side of the wall 1426 is a long recess 1428.

Figure 23:
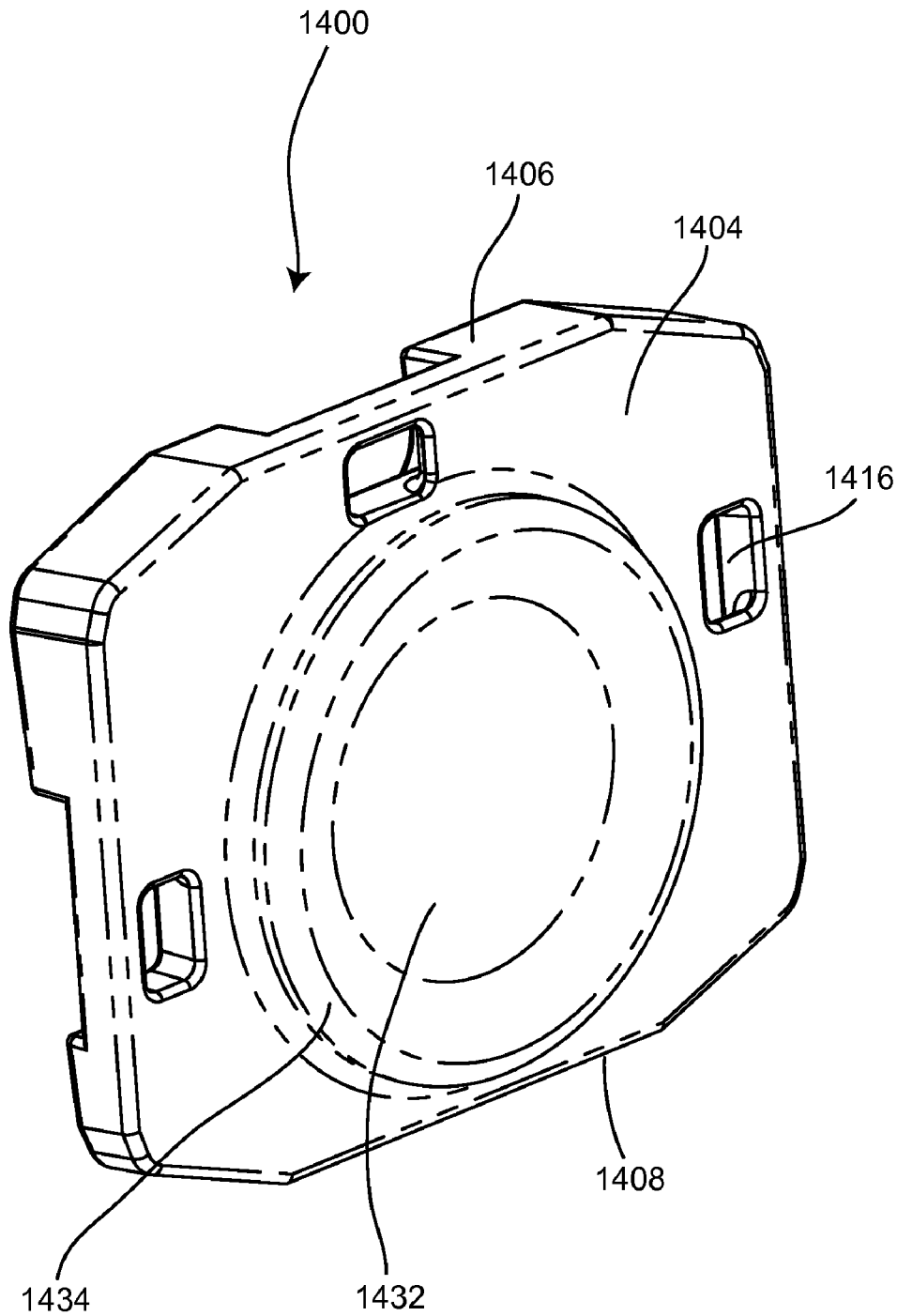
FIG. 23 is a perspective view of a caudal side of the superior bearing shown in FIG. 17.

Referring to FIG. 23, the caudal side 1404 of the superior bearing 1400 is shown. The three instrument ports 1416 open out on the caudal side 1404. A circular ridge 1434 rises from the caudal side 1404 of the superior bearing 1400. In the center of the circle formed by the ridge 1434, a cup 1432 is depressed into the superior bearing 1400. The cup 1432 on the superior bearing 1400 and the dome 1432 on the inferior bearing 1300 form the bearing surfaces when the implant 1050 is implanted.

Figure 24:
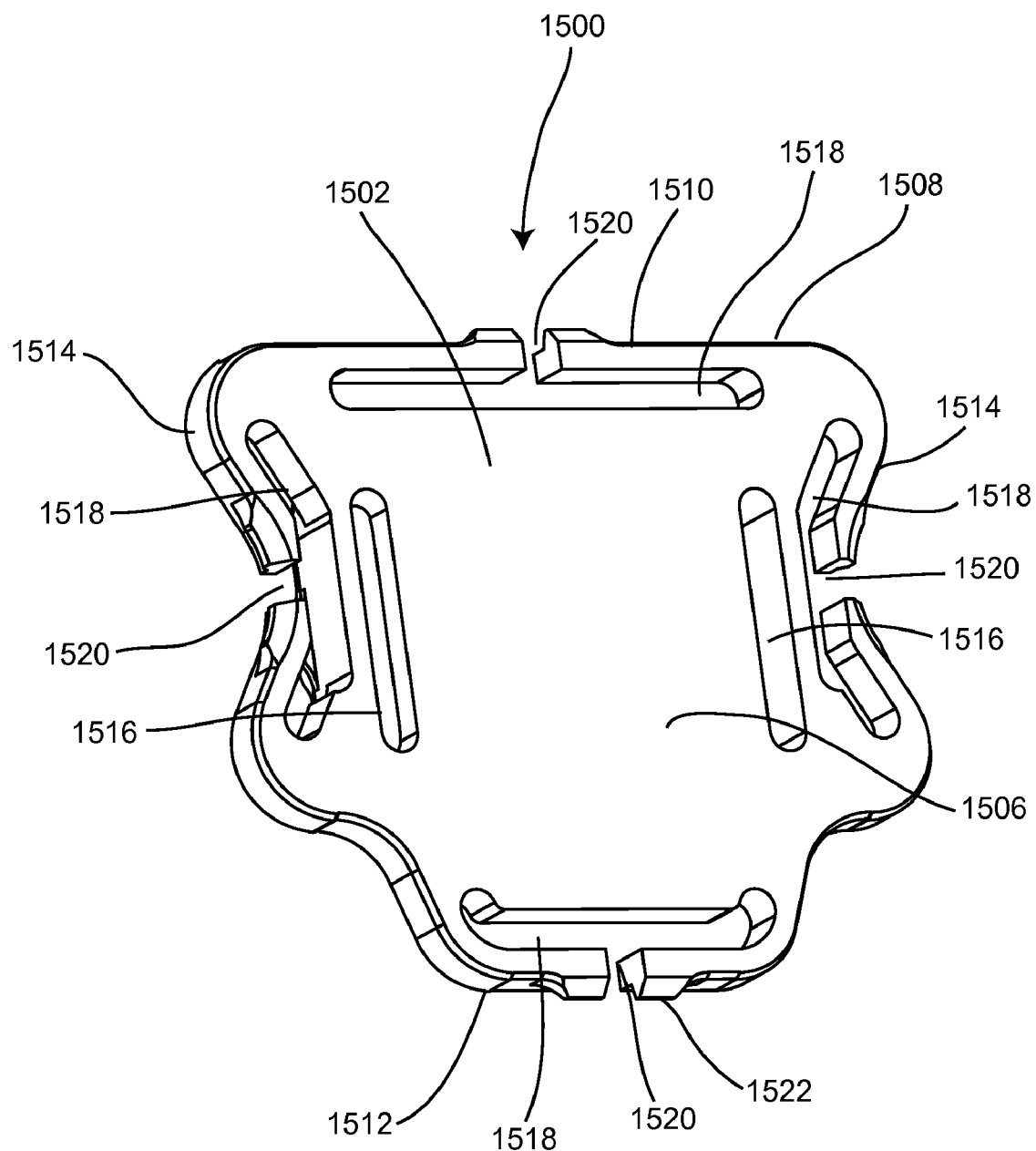
FIG. 24 is a perspective view of a bone-facing side of the snap fastener shown in FIG. 17.

Referring to FIG. 24, a bone-facing side 1502 of one snap fastener 1500 is shown. The bone-facing side 1502 is flat and has a generally square shape, with a central body 1506 and an irregular outer edge 1508. The snap fastener has an anterior end 1510, a posterior end 1512, and two lateral sides 1514. Two connection slots 1516 perforate the snap fastener, each generally parallel to a lateral side 1512 of the body 1506. Four connection ports 1518 are located just inside the outer edge 1508, one each on the anterior and posterior ends 1510, 1512, and one on each lateral side 1514. There is a gap 1520 in the outer edge 1508 adjacent to each connection port 1518, such that the outer edge 1508 is not continuous but each connection port 1518 has an opening to the outside of the fastener 1500. Formed onto the outer edge 1508 immediately adjacent to each gap 1520 is a tab 1522, each tab 1522 being a protrusion from the outer edge 1508, extending in the same plane as the body 1506.

Figure 25:
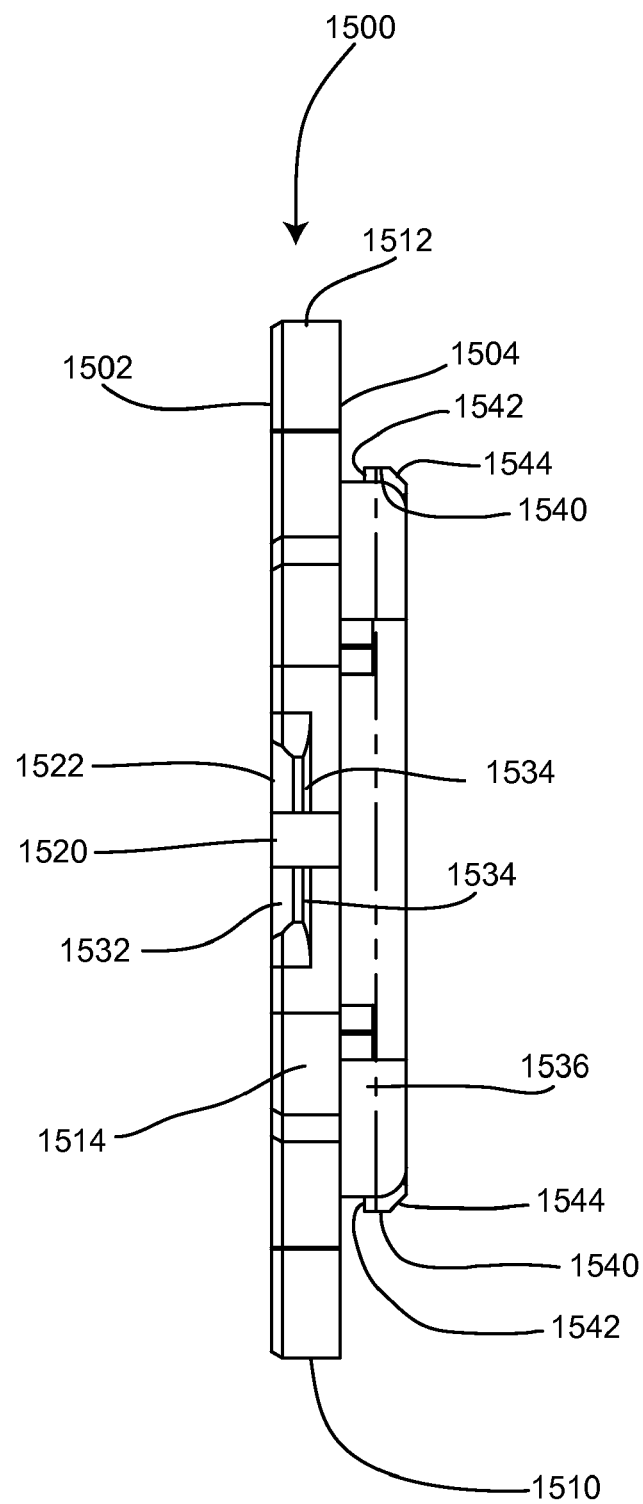
FIG. 25 is an enlarged perspective side view of the snap fastener shown in FIG. 17.

Referring to FIG. 25, an enlarged side view of a snap fastener 1500 is shown, in order to depict the tabs 1522 in greater detail. Each tab 1522 has a sloped bone-facing side 1532 and a sloped bearing-facing side 1534. The slope of the bearing-facing side 1534 is steeper than the slope of the bone-facing side 1532. This is so that when the tabs 1522 are snapped into the recesses 1134 in the walls 1132 of the end plate 1100, more force is required to remove the snap fastener 1500 from the end plate 1100 than it takes to snap the snap fastener 1500 to the end plate 1100 or 1200.

Figure 26:
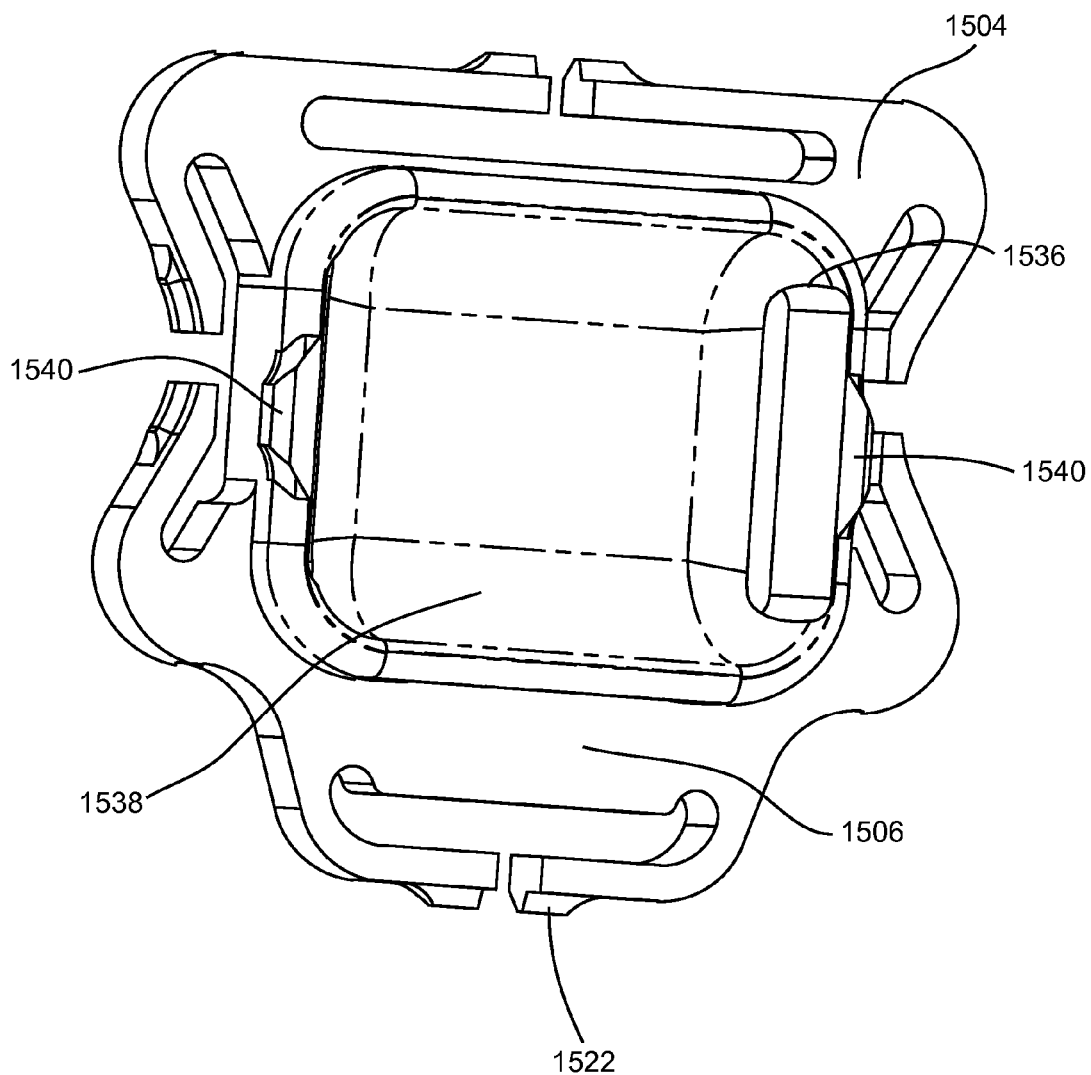
FIG. 26 is a perspective view of a bearing-facing side of the snap fastener shown in FIG. 17.

Referring to FIG. 26, a bearing-facing side 1504 of the snap fastener 1500 is shown. In the center of the body 1506, a raised rim 1536 surrounds a rectangular dish 1538. Protruding on each lateral side of the rim 1536 is a long tab 1540. The long tabs 1540 are configured to fit into the long recesses 1328, 1428 on the bearings 1300, 1400 when the snap fastener 1500 is snapped to the bearing. Returning to FIG. 25, each long tab 1540 has a bone-facing side 1542 and a bearing-facing side 1544. The slope of the bone-facing side 1542 is 90 degrees, and the slope of the bearing-facing side 1544 is less steep, approximating 45 degrees. This is so that when the snap fastener 1500 is snapped on to the inferior or superior bearing 1300, 1400, it will require considerably less force to snap the fastener 1500 on the bearing than to remove it.

When the snap fastener 1500 is snapped on to the end plate 1100, the bone-facing side 1532 of the tab 1522 pushes against the bearing-facing side 1104 of the end plate 1100, and the outer edge 1508 flexes slightly until the tab 1522 is forced into the recess 1134. Since the slope on the bearing-facing side 1534 of the tab 1522 is steeper, it would take much more force to remove the tab 1522 from the recess 11134.

The present invention may be embodied in other specific forms without departing from its spirit or essential characteristics. It is appreciated that various features of the above-described examples can be mixed and matched to form a variety of other alternatives, each of which may have a different bearing set, fusion block, or snap connection system according to the invention. As such, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An intervertebral implant comprising:
a first end plate configured to be secured to a first vertebral body adjacent to an intervertebral space; and
a first intermediate component lockable into a rigidly locked position in which the first end plate and the first intermediate component are rigidly locked together in response to motion between the first intermediate component and the first end plate, wherein the first intermediate component comprises a concave articular surface positioned to provide post-operative articulation with an adjacent surface when the first intermediate component is locked in the rigidly locked position.

2. The intervertebral implant of claim 1, wherein the first intermediate component is positionable in a free position relative to the first end plate, wherein in the free position, relative motion between the first intermediate component and the first end plate is unrestricted, wherein the first intermediate component is movable between the locked and free positions along a straight pathway having a length of 6 millimeters or less.

3. The intervertebral implant of claim 2, wherein a first force required to lock the first intermediate component into the locked position relative to the first end plate is less than a second force required to move the first intermediate component from the locked position to the free position relative to the first end plate.

4. The intervertebral implant of claim 1, wherein a force required to lock the first intermediate component into the locked position relative to the first end plate is 20 pounds or less.

5. The intervertebral implant of claim 1, wherein the first intermediate component is further configured to be locked in response to motion of the first intermediate component toward the first end plate along a cephalad-caudal path.

6. The intervertebral implant of claim 1, further comprising:
a second end plate configured to be secured to a second vertebral body adjacent to the intervertebral space; and
a second intermediate component configured to be lockable into a locked position relative to the second end plate in response to motion between the second intermediate component and the second end plate, wherein the second intermediate component comprises a convex articular surface shaped to articulate with the concave articular surface.

7. The intervertebral implant of claim 6, further comprising a third intermediate component configured to be lockable into a locked position relative to the first and second end plates in response to motion between the third intermediate component and the first and second end plates, wherein the third intermediate component comprises a fusion block configured to substantially prevent relative motion between the first and second end plates.

8. The intervertebral implant of claim 1, further comprising a snap fastener separate from the first end plate and the first intermediate component, wherein the snap fastener is shaped to be secured to the first intermediate component and to snap into engagement with the first end plate.

9. The intervertebral implant of claim 1, wherein the first intermediate component is configured to be lockable into the locked position after the first end plate is secured to the first vertebral body, and without detaching the first end plate from the first vertebral body.

10. The intervertebral implant of claim 1, wherein the first end plate comprises at least one anchoring member shaped to penetrate the first vertebral body to secure the first end plate to the first vertebral body.

11. An intervertebral implant comprising:
a first end plate configured to be secured to a first vertebral body adjacent to an intervertebral space;
a second end plate configured to be secured to a second vertebral body adjacent to the intervertebral space;
a compressible tapered wall comprising a compressed configuration and a relaxed configuration; and
a first intermediate component formed separately from the first and second end plates, wherein the first intermediate component is reversibly lockable into a locked position relative to the first end plate in response to reversion of the tapered wall from the compressed configuration to the relaxed configuration.

12. The intervertebral implant of claim 11, wherein the first intermediate component further comprises a free position relative to the first end plate, wherein in the free position, relative motion between the first intermediate component and the first end plate is unrestricted, wherein the first intermediate component is movable between the locked and free positions along a straight pathway having a length of 6 millimeters or less.

13. The intervertebral implant of claim 12, wherein a first force required to lock the first intermediate component into the locked position relative to the first end plate is less than a second force required to move the first intermediate component from the locked position to the free position relative to the first end plate.

14. The intervertebral implant of claim 11, wherein a force required to lock the first intermediate component into the locked position relative to the first end plate is 20 pounds or less.

15. The intervertebral implant of claim 11, wherein the first intermediate component comprises a concave articular surface, the intervertebral implant further comprising:
a second intermediate component lockable into a locked position relative to the second end plate in response to motion between the second intermediate component and the second end plate, wherein the second intermediate component comprises a convex articular surface shaped to articulate with the concave articular surface.

16. The intervertebral implant of claim 15, further comprising a third intermediate component configured to be lockable into a locked position relative to the first and second end plates in response to motion between the third intermediate component and the first and second end plates, wherein the third intermediate component comprises a fusion block configured to substantially prevent relative motion between the first and second end plates.

17. The intervertebral implant of claim 11, further comprising a snap fastener separate from the first end plate and the first intermediate component, the snap fastener comprising the tapered wall, wherein the snap fastener is shaped to be secured to the first intermediate component and to snap into engagement with the first end plate.

18. The intervertebral implant of claim 11, wherein the first intermediate component is configured to be lockable into the locked position after the first end plate is secured to the first vertebral body, and without detaching the first end plate from the first vertebral body.

19. The intervertebral implant of claim 11, wherein the first end plate comprises at least one anchoring member shaped to penetrate the first vertebral body to secure the first end plate to the first vertebral body.

20. The intervertebral implant of claim 19, wherein each anchoring member is shaped to define a channel extending therethrough.

21. A method of implanting an intervertebral implant on a spine comprising a first vertebral body adjacent to an intervertebral space, the method comprising:
securing a first end plate to the first vertebral body;
moving a first intermediate component to a rigidly locked position relative to the first end plate in which the first end plate and the first intermediate component are rigidly locked together after securing the first end plate to the first vertebral body, the first intermediate component comprising a concave articular surface; and
locking the first intermediate component in the locked position relative to the first end plate in response to the relative motion, wherein after locking the first intermediate component in the rigidly locked position, the concave articular surface is positioned to provide post-operative articulation with the adjacent surface.

22. The method of claim 21, wherein moving the first intermediate component to the locked position comprises moving the first intermediate component from a free position along a straight pathway to the locked position, the straight pathway having a length of 6 millimeters or less, wherein, in the free position, relative motion between the first intermediate component and the first end plate is unrestricted.

23. The method of claim 22, wherein moving the first intermediate component to the locked position comprises exerting a first force on the first intermediate component, wherein the first force is less than a second force that would be required to move the first intermediate component from the locked position to the free position.

24. The method of claim 21, wherein moving the first intermediate component to the locked position comprises exerting a first force on the intermediate component, wherein the first force is 20 pounds or less.

25. The method of claim 21, wherein moving the first intermediate component to the locked position comprises moving the first intermediate component toward the first end plate along a cephalad-caudal path.

26. The method of claim 21, further comprising:
securing a second end plate to a second vertebral body adjacent to the intervertebral space; and
moving a second intermediate component to a locked position relative to the second end plate, the second intermediate component comprising a convex articular surface shaped to articulate with the concave articular surface; and
locking the second intermediate component in the locked position relative to the second end plate in response to the relative motion.

27. The method of claim 26, further comprising:
detaching the first intermediate component from the first end plate;
detaching the second intermediate component from the second end plate;
moving a third intermediate component to a locked position relative to the first and second end plates; and
locking the third intermediate component into a locked position relative to the first and second end plates in response to the relative motion;
wherein the third intermediate component comprises a fusion block configured to substantially prevent relative motion between the first and second end plates.

28. The method of claim 21, further comprising securing a snap fastener to the first intermediate component; wherein locking the first intermediate component in the locked position comprises snapping the snap fastener into engagement with the first end plate.

29. The method of claim 21, wherein locking the first intermediate component in the locked position is carried out without detaching the first end plate from the first vertebral body.

30. The method of claim 21, wherein securing the first end plate to the first vertebral body comprises penetrating the first vertebral body with at least one anchoring member.

31. A method of implanting an intervertebral implant on a spine comprising a first vertebral body adjacent to an intervertebral space, the method comprising:
securing a first end plate to the first vertebral body;
moving a first intermediate component along a cephalad-caudal path to a locked position relative to the first end plate after the first end plate has been secured to the first vertebral body;
reverting a compressible tapered wall from a compressed configuration to a relaxed configuration in response to the relative motion; and
reversibly locking the first intermediate component in the locked position relative to the first end plate in response to the reversion of the tapered wall from the compressed configuration to the relaxed configuration.

32. The method of claim 31, wherein moving the first intermediate component to the locked position comprises moving the first intermediate component from a free position along a straight pathway to the locked position, the straight pathway having a length of 6 millimeters or less, wherein, in the free position, relative motion between the first intermediate component and the first end plate is unrestricted.

33. The method of claim 32, wherein moving the first intermediate component to the locked position comprises exerting a first force on the first intermediate component, wherein the first force is less than a second force that would be required to move the first intermediate component from the locked position to the free position.

34. The method of claim 31, wherein moving the first intermediate component to the locked position comprises exerting a first force on the intermediate component, wherein the first force is 20 pounds or less.

35. The method of claim 31, wherein the first intermediate component comprises a concave articular surface, the method further comprising:
   securing a second end plate to a second vertebral body adjacent to the intervertebral space; and
   moving a second intermediate component to a locked position relative to the second end plate, the second intermediate component comprising a convex articular surface shaped to articulate with the concave articular surface; and
   locking the second intermediate component in the locked position relative to the second end plate in response to the relative motion.

36. The method of claim 35, further comprising:
   detaching the first intermediate component from the first end plate;
   detaching the second intermediate component from the second end plate;
   moving a third intermediate component to a locked position relative to the first and second end plates; and
   locking the third intermediate component into a locked position relative to the first and second end plates in response to the relative motion;
   wherein the third intermediate component comprises a fusion block configured to substantially prevent relative motion between the first and second end plates.

37. The method of claim 31, further comprising securing a snap fastener to the first intermediate component; wherein locking the first intermediate component in the locked position comprises snapping the snap fastener into engagement with the first end plate.

38. The method of claim 31, wherein locking the first intermediate component in the locked position is carried out after securement of the first end plate to the first vertebral body; wherein locking the first intermediate component in the locked position is carried out without detaching the first end plate from the first vertebral body.

39. The method of claim 31, wherein securing the first end plate to the first vertebral body comprises penetrating the first vertebral body with at least one anchoring member.

* * * * *